US012660818B2

(12) United States Patent
Al-Babili et al.

(10) Patent No.: US 12,660,818 B2
(45) Date of Patent: *Jun. 23, 2026

(54) STRIGOLACTONE ANALOGS AND METHODS OF USING

(71) Applicants: King Abdullah University of Science and Technology, Thuwal (SA); University of Tokyo, Tokyo (JP)

(72) Inventors: Salim Al-Babili, Thuwal (SA); Tadao Asami, Tokyo (JP)

(73) Assignee: King Abdullah University of Science and Technology, Thuwal (SA)

( * ) Notice: Subject to any disclaimer, the term of this patent is extended or adjusted under 35 U.S.C. 154(b) by 975 days.

This patent is subject to a terminal disclaimer.

(21) Appl. No.: 17/779,699

(22) PCT Filed: Nov. 25, 2020

(86) PCT No.: PCT/IB2020/061146

§ 371 (c)(1),
(2) Date: May 25, 2022

(87) PCT Pub. No.: WO2021/105898

PCT Pub. Date: Jun. 3, 2021

(65) Prior Publication Data

US 2023/0054152 A1 Feb. 23, 2023

Related U.S. Application Data

(60) Provisional application No. 62/939,965, filed on Nov. 25, 2019.

(51) Int. Cl.
*A01N 43/08* (2006.01)
*C07D 307/60* (2006.01)

(52) U.S. Cl.
CPC ........... *A01N 43/08* (2013.01); *C07D 307/60* (2013.01)

(58) Field of Classification Search
CPC .................................................... C07D 307/60
See application file for complete search history.

(56) References Cited

U.S. PATENT DOCUMENTS

| | | | | |
|---|---|---|---|---|
| 4,976,769 | A | 12/1990 | Iwasaki | |
| 8,980,795 | B2 * | 3/2015 | Al-Babili | C07D 307/58 504/299 |
| 9,326,510 | B2 * | 5/2016 | Al-Babili | C12P 17/04 |
| 11,903,386 | B2 * | 2/2024 | Al-Babili | A01N 43/08 |
| 2007/0105721 | A1 | 5/2007 | Flematti | |
| 2010/0048516 | A1 | 2/2010 | Baur | |

FOREIGN PATENT DOCUMENTS

| | | |
|---|---|---|
| EP | 0579052 | 1/1994 |
| WO | 2005104844 | 11/2005 |
| WO | 2018050477 | 3/2018 |
| WO | 2018060865 | 4/2018 |

OTHER PUBLICATIONS

Al-Babili et al (2018 ): STN International, Caplus database, Accession No. 2018 : 689944.*
Mori , et al., "Carlactone-type strigolactones and their synthetic analogues as inducers of hyphal branching in arbuscular mycorrhizal fungi", Phytochemistry, vol. 130, Jun. 2, 2016, pp. 90-98.
Abe, et al., "Carlactone is converted to carlactonoic acid by MAX1 in *Arabidopsis* and its methyl ester can directly interact with AtD14 in vitro", PNAS, 111:18084-18089 (2014).
Abuauf, et al., "The *Arabidopsis* DWARF27 gene encodes an all-trans-/9-cis-β-carotene isomerase and is induced by auxin, abscisic acid and phosphate deficiency", Plant Science, 277:33-42 (2018).
Agusti, et al., "Strigolactone signaling is required for auxin-dependent stimulation of secondary growth in plants", PNAS, 108(50):20242-20247 (2011).
Akiyama, et al., "Plant sesquiterpenes induce hyphal branching in arbuscular mycorrhizal fungi", Nature, 435(7043):824-827 (2005).
Al-Babili, et al., "Strigolactones, a novel carotenoid-derived plant hormone", Annual Review of Plant Biology, 66:161-186 (2015).
Arite, et al., "d14, a strigolactone-insensitive mutant of rice, shows an accelerated outgrowth of tillers", Plant and Cell Physiology, 50(8):1416-1424 (2009).
Bonfante, et al., "Mechanisms underlying beneficial plant—fungus interactions in mycorrhizal symbiosis", Nature Comm., 1:48, 11 pages (2010).
Boyer, et al., "New Strigolactone analogs as plant hormones with low activities in the rhizosphere", Molecular Plant, 7(4):675-690 (2014).
Bruno, et al., "Insights into the formation of carlactone from in-depth analysis of the CCD8-catalyzed reactions", FEES letters, 591(5):792-800 (2017).
Bruno, et al., "On the substrate specificity of the rice strigolactone biosynthesis enzyme DWARF27", Planta, 243(6):1429-1440 (2016).
Bruno, et al., "On the substrate- and stereospecificity of the plant carotenoid cleavage dioxygenase 7", FEBS Letters, 588(9):1802-1807 (2014).
Charnikhova, et al., "Zealactones. Novel natural strigolactones from maize", Phytochemistry, 137:123-131 (2017).

(Continued)

*Primary Examiner* — Golam M Shameem
(74) *Attorney, Agent, or Firm* — Pabst Patent Group LLP

(57) ABSTRACT

Disclosed herein are compounds and methods for regulating plant growth and/or combating root parasitic plants. Formulations containing one or more disclosed compounds or salts thereof, and one or more excipients are disclosed. Methods for regulating plant growth typically includes applying one or more formulations to a plant, a plant part, or a growing site of plant, where the one or more compounds or salts thereof can be in an effective amount to inhibit tillering, trigger senescence, and/or cause stunted growth of the plant. The plant can be a cereal, grain, or vegetable plant. Methods for combating root parasitic plants typically includes applying one or more formulations to a root parasitic plant, a plant part of root parasitic plant, or a growing site of root parasitic plant, where the one or more compounds or salts thereof can be in an effective amount to induce parasitic seed germination.

15 Claims, 8 Drawing Sheets

(56) References Cited

OTHER PUBLICATIONS

Decker, et al., "Strigolactone biosynthesis is evolutionarily conserved, regulated by phosphate starvation and contributes to resistance against phytopathogenic fungi in a moss, Physcomitrella patens", New Phytologist, 216(2):455-468 (2017).
Ejeta, "Breeding for Striga Resistance in Sorghum: Exploitation of an Intricate Host—Parasite Biology", Crop Science, 47:216-227 (2007).
Fukui, et al., "New branching inhibitors and their potential as strigolactone mimics in rice", Bioorg & Med Chem Lett., 21(16):4905-4908 (2011).
Fukui, et al., "Selective mimics of strigolactone actions and their potential use for controlling damage caused by root parasitic weeds", Molecular Plant, 6(1):88-99 (2013).
Gomez-Roldan, et al., "Strigolactone inhibition of shoot branching", Nature, 455(7210):189-194 (2008).
Gressel, et al., "Major heretofore intractable biotic constraints to African food security that may be amenable to novel biotechnological solutions", Crop Protection, 23:661-689 (2004).
Gutjahr, et al., "Cell and developmental biology of arbuscular mycorrhiza symbiosis", Ann. Rev. Cell and Dev. Biol., 29:93-617 (2013).
Ha, et al., "Positive regulatory role of strigolactone in plant responses to drought and salt stress", PNAS, 111(2):851-856 (2013).
International Search Report for PCT/IB2020/061146 dated Jan. 26, 2021.
Jamil, et al., "Methyl phenlactonoates are efficient strigolactone analogs with simple structure", Journal of Experimental Botany, 69(9):62319-62331 (2018).
Jamil, et al., "Striga hermonthica parasitism in maize in response to N and P fertilisers", Field Crops Research, 134:1-10 (2012a).
Jia, et al., "From carotenoids to strigolactones", Journal of Experimental Botany, 69(9):2189-2204 (2018).
Jia, et al., "Nitro-Phenlactone, a Carlactone Analog with Pleiotropic Strigolactone Activities", Molecular Plant, 9(9):1341-1344 (2016).
Kgosi, et al., "Strigolactone analogues induce suicidal seed germination of *Striga* spp. in soil", Weed Research, 52(3):197-203 (2012).
Kondo, et al., "Synthesis and seed germination stimulating activity of some imino analogs of strigolactones", Bioscience Biotech. and Biochem., 71(11): 2781-2786 (2007).
Kountche, et al., "Suicidal germination as a control strategy for Striga hermonthica(Benth.) in smallholder farms of sub_Saharan Africa", Plants, People, Planet, 1:107-118 (2019).
Mangnus, et al., "Structural modifications of strigol analogs. Influence of the B and C rings on the bioactivity of the germination stimulant GR24", J. of Agric. and Food Chem., 40:1222-1229 (1992c).
Rasmussen, et al., "A fluorescent alternative to the synthetic strigolactone GR24", Molecular Plant, 6(1):100-112 (2013).
Rodenburg, et al., "Parasitic weed incidence and related economic losses in rice in Africa", Agric., Ecosystems & Environ., 235:306-317 (2016).
Rubiales, et al., "Revisiting strategies for reducing the seedbank of *Orobanche* and *Phelipanche* spp", Weed Research, 49 (Suppl. 1):23-33 (2009).
Ruyter-Spira, et al., "Physiological effects of the synthetic strigolactone analog GR24 on root system architecture in *Arabidopsis*: another belowground role for strigolactones?", Plant Physiology, 155(2):721-734 (2011).
Samejima, et al., "Practicality of the suicidal germination approach for controlling Striga hermonthica", Pest Management Science, 72(11):2035-2042 (2016).
Scaffidi, et al., "Strigolactone Hormones and Their Stereoisomers Signal through Two Related Receptor Proteins to Induce Different Physiological Responses in *Arabidopsis*", Plant Physiology, 165(3):1221-1232 (2014).
Seto, et al., "Carlactone is an endogenous biosynthetic precursor for strigolactones", PNAS, 111(4):1640-1645 (2014).
Toh, et al., "Structure-function analysis identifies highly sensitive strigolactone receptors in Striga", Science, 350(6257):203-207 (2015).
Tsuchiya, et al., "Parasitic Plants. Probing strigolactone receptors in Striga hermonthica with fluorescence", Science, 349(6250): 864-868 (2015).
Ueno, et al., "Heliolactone, a non-sesquiterpene lactone germination stimulant for root parasitic weeds from sunflower", Phytochemistry, 108:122-128 (2014).
Umehara, et al., "Inhibition of shoot branching by new terpenoid plant hormones", Nature, 455(7210):195-200 (2008).
Wang, et al., "The apocarotenoid metabolite zaxinone regulates growth and strigolactone biosynthesis in rice", Nature Communication, 10(1):810, 9 pages (2019).
Waters, et al., "Strigolactone Signaling and Evolution", Annual Review of Plant Biology, 68:291-322 (2017).
Wigchert, et al., "Dose-response of seeds of the parasitic weeds Striga and Orobanche toward the synthetic germination stimulants GR 24 and Nijmegen 1", Journal of Agric. and Food Chem., 47(4):1705-1710 (1999).
Yamada, et al., "Strigolactone signaling regulates rice leaf senescence in response to a phosphate deficiency", Planta, 240(2):399-408 (2014).
Yao, et al., "Dwarf14 is a non-canonical hormone receptor for Strigolactone", Nature, 536:469-473 (2016).
Yasui, et al., "Total synthesis of avenaol", Nature Communications, 8(1):674-683 (2017).
Zhang, et al., "Rice cytochrome P450 MAX1 homologs catalyze distinct steps in strigolactone biosynthesis", Nature Chemical Biology, 10(12):1028-1033 (2014).
Zwanenburg, et al., "New strigolactone mimics: structure-activity relationship and mode of action as germinating stimulants for parasitic weeds", Bioorganic & Med. Chem. Lett., 23(18):5182-5186 (2013a).
Zwanenburg, et al., "Strigolactones: new plant hormones in action", Planta, 243(6):1311-1326 (2016b).
Zwanenburg, et al., "Structure and activity of strigolactones: new plant hormones with a rich future", Molecular Plant, 6(1):38-62 (2013b).
Zwanenburg, et al., "Structure and function of natural and synthetic signalling molecules in parasitic weed germination", Pest Management Science, 6(5):478-491 (2009).

* cited by examiner

STRIGOLACTONE ANALOGS AND METHODS OF USING

CROSS-REFERENCE TO RELATED APPLICATIONS

The present application is a National Phase application under 35 U.S.C. 371 of PCT/IB2020/061146, filed Nov. 25, 2020, which claims the benefit of and priority to U.S. Provisional Application No. 62/939,965 filed Nov. 25, 2019, the disclosures of which are incorporated herein by reference in their entirety.

FIELD OF THE INVENTION

The invention is generally directed to Strigolactone analogs and methods for using the Strigolactone analogs to regulate plant growth and combat root parasitic plants.

BACKGROUND OF THE INVENTION

Strigolactones (SLs) are well known carotenoid derived metabolites that act as endogenous phyto-hormones as well as rhizospheric signaling molecules. As plant hormones, SLs are involved in controlling shoot branching/tillering, root architecture and contribute to further aspects of plant growth, as well as to pathogen defense and abiotic stress responses (Gomez-Roldan et al., 2008; Umehara et al., 2008; Agusti et al., 2011; Kapulnik et al., 2011; Ruyter-Spira et al., 2011; Ha et al., 2014; Decker et al., 2017). Upon release into the rhizosphere, SLs stimulate the metabolism of AM fungi (AMP) and induce germination of their spores and branching of their hyphae (Bonfante and Genre, 2010; Gutjahr and Parniske, 2013). These changes pave the way for establishing the beneficial AM symbiosis, in which AMF help host plants to uptake mineral nutrients and water through a wide net of extraradical fungal hyphae, and obtain in return sugars and other reduced carbon compounds (Akiyama et al., 2005; Bonfante and Genre, 2010). However, released SLs are also sensed by seeds of root parasitic plants (weeds), which use SLs as germination stimulant. These weeds cause enormous losses in yields of several crop species (Cook et al., 1966). In particular, root parasitic plants of the genus *Striga* are considered as one of the major biotic constraints and threats to global food security, devastating cereal production in Africa. It has been reported that severe infestation of *Striga* results 50% to complete crop failure, affecting the life of 300 million people and causing 7 billion US $ loss annually (Gressel et al., 2004; Ejeta, 2007). *Striga* infestation is spreading over 50 million ha of land in 32 African countries (Rodenburg et al., 2016).

The isolation and organic synthesis of natural SLs in large quantities is very difficult because of their complex structure and their scarce amount in plant tissues and root exudates (Zwanenburg et al., 2016b; Zwanenburg et al., 2016c). Therefore, SL fundamental research, as well as agricultural application, has been heavily relying on synthetic SL analogs. In 1981, the common canonical SL analog GR24 with ABC-ring coupled to the D-ring was developed and since then, has been widely used in labs for SL and root parasitic weed research (Johnson et al., 1981; Mangnus and Zwanenburg, 1992). However, large scale synthesis of GR24 is very expensive and laborious because of its many synthesis steps (Mangnus et al., 1992a; Rasmussen et al., 2013).

There remains a need for SL analogs that are characterized by simple synthesis.

Therefore, it is the object of the present invention to provide SL analogs.

It is another object of the present invention to provide methods of using the SL analogs.

SUMMARY OF THE INVENTION

Disclosed herein are compounds having a structure of Formula I:

Formula I

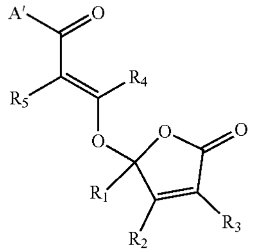

(a) where A' is an alkoxy group containing one substituent, an amino group optionally containing one or two substituents at the amino nitrogen, or a thiol group optionally containing one substituent at the thiol sulfur;

(b) where $R_1$-$R_4$ are independently a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group; and (c) where $R_5$ is an unsubstituted alkyl group, a substituted alkyl group, an unsubstituted cycloalkyl group, a substituted cycloalkyl group, an unsubstituted heteroalkyl group, a substituted heteroalkyl group, an unsubstituted cycloheteroalkyl group, a substituted cycloheteroalkyl group, an unsubstituted alkenyl group, a substituted alkenyl group, an unsubstituted heteroalkenyl group, a substituted heteroalkenyl group, a substituted alkynyl group, a substituted heteroalkynyl group, an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, or a substituted polyheteroaryl group, an unsubstituted alkylaryl group, or a substituted alkylaryl group.

In some embodiments, the compound can have a structure of Formula

Formula III

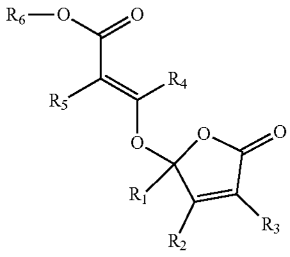

(a) where $R_1$-$R_4$ are independently a hydrogen atom, a halogen atom, an alkyl group, a hydroxyl group, or an amino group; and (b) where $R_5$ and $R_6$ are independently an unsubstituted aryl group, a substituted aryl group, an unsubstituted polyaryl group, a substituted polyaryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

In some embodiments, the compound can have a structure of Formula VI:

Formula VI

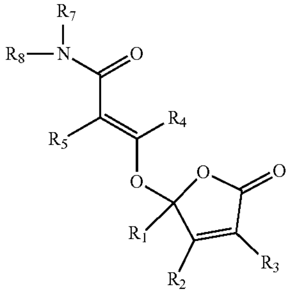

(a) where $R_1$-$R_4$ are as defined above;

(b) where $R_5$ is an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group; and (c) where $R_7$ and $R_8$ are independently a hydrogen atom, an unsubstituted alkyl group, a substituted alkyl group, an unsubstituted heteroalkyl group, a substituted heteroalkyl group, an unsubstituted alkenyl group, a substituted alkenyl group, an unsubstituted heteroalkenyl group, a substituted heteroalkenyl group, an unsubstituted alkynyl group, a substituted alkynyl group, an unsubstituted heteroalkynyl group, a substituted heteroalkynyl group, an unsubstituted aryl group, a substituted aryl group, an unsubstituted an unsubstituted heteroaryl group, or a substituted heteroaryl group, where the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

Formulations containing one or more of the disclosed compounds or salts thereof, and one or more excipients are disclosed.

The formulation excipient can be a solid carrier, a liquid carrier, or a surface-active agent.

Methods for using the one or more compounds or salts thereof, and one or more formulations are also disclosed. The compounds and formulations are used to regulate plant growth and/or induce parasitic germination.

A method for regulating plant growth typically includes applying one or more formulations to a plant, a plant part, or a growing site of plant, where the one or more compounds or salts thereof in the one or more formulations are in an effective amount to regulate plant growth.

In some embodiments, the one or more compounds or salts thereof in the one or more formulations are in an effective amount to inhibit tillering of the plant and/or trigger dark-induced leaf senescence. In some embodiments, the one or more compounds or salts thereof in the one or more formulations are in an effective amount to cause stunted growth and/or trigger senescence in the plant or plant part (e.g. seedling or seeds of the plant), leading to reduced biomass and/or plant height.

The plant can be a cereal, grain, or vegetable plant. The plant can be seedling or mature plant. The plant part can be seed, leaf, or root of the plant.

A method for combating root parasitic plants typically includes applying one or more formulations to a root parasitic plant, a plant part of root parasitic plant, or a growing site of root parasitic plant, where the one or more compounds or salts thereof are in an effective amount to induce parasitic seed germination.

The parasitic weed can be a *Striga* species or a *B. aegyptiaca* species of the Zygophyllaceae family.

The compounds disclosed herein can be prepared via simple synthesis, and are highly effective in regulating plant growth (e.g., reducing number of tillering and dry biomasses and triggering dark-induced leaf senescence), and/or combating root parasitic plants. In some embodiments, the disclosed compounds can have higher efficiency in regulating plant architecture, (e.g., reducing number of tillering and dry biomasses, and/or triggering dark-induced leaf senescence), and/or inducing parasitic seed germination (e.g., *Striga, P. aegptiaca*), compared to that of widely applied SL analog GR24.

BRIEF DESCRIPTION OF THE DRAWINGS

FIG. 1A is a bar graph showing number of tillers per plant counted after three weeks of MP compounds application. FIG. 1B is a bar graph showing dry biomass of d10 rice seedlings, measured after three weeks of MP compounds application. Data are means±SE (n=8). Means not sharing a letter in common differ significantly at $P_{0.05}$.

FIG. 2A is a bar graph showing number of tillers per plant counted after three weeks of MP compounds application. FIG. 2B is a bar graph showing dry biomass of d3 rice seedlings measured after three weeks of MP compounds application. Data are means±SE (n=8). Means not sharing a letter in common differ significantly at $P_{0.05}$.

FIG. 4A is a bar graph showing daily effect on chlorophyll content. FIG. 4B is a bar graph showing daily effect on membrane ion leakage. Data are means±SE (n=6). Means not sharing a letter in common differ significantly at $P_{0.05}$.

DETAILED DESCRIPTION OF THE INVENTION

I. Compositions

A. Compounds

Figure 1A:
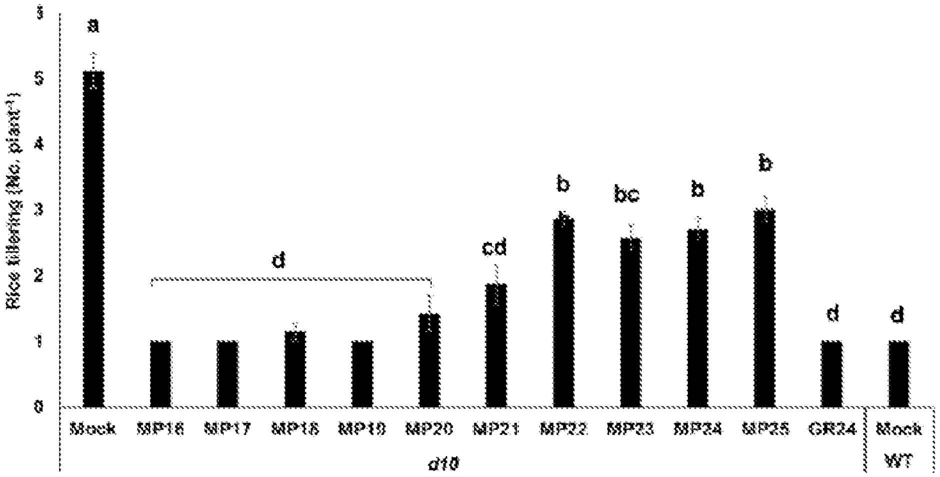
FIGS. 1A-1B are bar graphs showing tillering inhibition in SL deficient d10/CCD8 rice mutant by MP16-MP25.

SLs are a class of important plant hormones with an array of diverse functions including regulation of plant growth and development, adaptation to nutritional availability, contribution to biotic and abiotic stress responses, and communication with beneficial microorganisms and root parasitic plants However, the limited availability of SLs is a constraint in investigating their biology and a major obstacle on the way towards their application at a large scale in agriculture. The development of easy-to-synthesize, low cost SL analogs/mimics with improved bioactivity is a key in solving problem. Designing of SL analogs that exert particular SL functions would be also a decisive step in translating fundamental SL research into application.

Up-till now GR24, which requires a complex synthesis protocol, is the widely used SL analog in labs (the structures of GR24 and ent-GR24 are shown below).

Disclosed herein are SL analogs that regulate plant growth and/or combat root parasitic plants. The SL analogs (or compounds) disclosed herein can be prepared via simple synthesis, and are highly effective in regulating plant growth (e.g., reducing number of tillering and dry biomasses, triggering dark-induced leaf senescence etc.), and/or combating root parasitic plants. In some embodiments, the disclosed compounds can have higher efficiency in regulating plant architecture, (e.g., reducing number of tillering and dry biomasses and/or triggering dark-induced leaf senescence), and/or inducing parasitic seed germination (e.g., *Striga, P. aegptiaca*), compared to that of widely applied SL analog GR24.

In particular, the disclosed compounds can have structures of Formula I.

Formula I

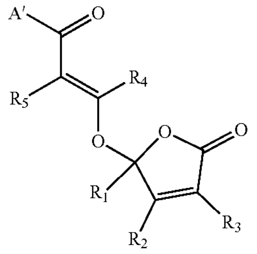

(a) where A' is an alkoxy group containing one substituent, an amino group optionally containing one or two substituents at the amino nitrogen, or a thiol group optionally containing one substituent at the thiol sulfur;

(b) where $R_1$-$R_4$ are independently a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group; and (c) where $R_5$ is an unsubstituted alkyl group, a substituted alkyl group, an unsubstituted cycloalkyl group, a substituted cycloalkyl group, an unsubstituted heteroalkyl group, a substituted heteroalkyl group, an unsubstituted cycloheteroalkyl group, a substituted cycloheteroalkyl group, an unsubstituted alkenyl group, a substituted alkenyl group, an unsubstituted heteroalkenyl group, a substituted heteroalkenyl group, a substituted alkynyl group, a substituted heteroalkynyl group, an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, or a substituted polyheteroaryl group, an unsubstituted alkylaryl group, or a substituted alkylaryl group.

In a substituted group or moiety, one or more hydrogen atoms in the chemical group or moiety is replaced with one or more substituents. Any substitution is in accordance with permitted valence of the substituted atom and the substituent, and that the substitution results in a stable compound, i.e., a compound that does not spontaneously undergo transformation such as by rearrangement, cyclization, elimination, etc. Suitable substituents include, but are not limited to a halogen atom, an alkyl group, a cycloalkyl group, a heteroalkyl group, a cycloheteroalkyl group, an alkenyl group, a heteroalkenyl group, an alkynyl group, a heteroalkynyl group, an aryl group, a heteroaryl group, a polyaryl group, a polyheteroaryl group, —OH, —SH, —$NH_2$, —$N_3$, —OCN, —NCO, —$ONO_2$, —CN, —NC, —ONO, —$CONH_2$, —NO, —$NO_2$, —$ONH_2$, —SCN, —SNCS, —$CF_3$, —$CH_2CF_3$, —$CH_2Cl$, —$CHCl_2$, —$CH_2NH_2$, —NHCOH, —CHO, —COCl, —COF, —COBr, —COOH, —$SO_3H$, —$CH_2SO_2CH_3$, —$PO_3H_2$, —$OPO_3H_2$, —P(═O)(OR$^{T1'}$)(OR$^{T2'}$), —OP(═O)(OR$^{T1'}$)(OR$^{T2'}$), —BR$^{T1'}$(OR$^{T2'}$), —B(OR$^{T1'}$)(OR$^{T2'}$), or -G'R$^{T1'}$ in which -T' is —O—, —S—, —NR$^{T2'}$—, —C(═O)—, —S(═O)—, —$SO_2$—, —C(═O)O—, —C(═O)NR$^{T2'}$—, —OC(═O)—, —NR$^{T2'}$C(═O)—, —OC(═O)O—, —OC(═O)NR$^{T2'}$—, —NR$^{T2'}$C(═O)O—, —NR$^{T2'}$C(═O)NR$^{T3'}$—, —C(═S)—, —C(═S)S—, —SC(═S)—, —SC(═S)S—, —C(═NR$^{T2'}$)—, —C(═NR$^{T2'}$)O—, —C(═NR$^{T2'}$)NR$^{T3'}$—, —OC(═NR$^{T2'}$)—, —NR$^{T2'}$C(═NR$^{T3'}$)—, —NR$^{T2'}$$SO_2$—, —C(═NR$^{T2'}$)NR$^{T3'}$—, —OC(═NR$^{T2'}$)—, —NR$^{T2'}$C(═NR$^{T3'}$)—, —NR$^{T2'}$$SO_2$—, —NR$^{T2'SO}$$_2$NR$^{T3'}$—, —NR$^{T2'}$C(═S)—, —SC(═S)NR$^{T2'}$—, —NR$^{T2'}$C(═S)S—, —NR$^{T2'}$C(═S)NR$^{T3'}$—, —SC(═NR$^{T2'}$)—, —C(═S)NR$^{T2'}$—, —OC(═S)NR$^{T2'}$—, —NR$^{T2'}$C(═S)O—, —SC(═O)NR$^{T2'}$—, —NR$^{T2'}$C(═O)S—, —C(═O)S—, —SC(═O)—, —SC(═O)S—, —C(═S)O—, —OC(═S)—, —OC(═S)O—, —$SO_2$NR$^{T2'}$—, —BR$^{T2'}$—, or —PR$^{T2'}$—; where each occurrence of R$^{T1'}$, R$^{T2'}$, and R$^{T3'}$ is, independently, a hydrogen atom, a halogen atom, an alkyl group, a heteroalkyl group, an alkenyl group, a heteroalkenyl group, an alkynyl group, a heteroalkynyl group, an aryl group, or a heteroaryl group.

In some embodiments, when A' in Formula I is an alkoxy group containing one substituent represented by Formula Ia and R' is not an alkyl group.

Formula Ia

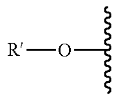

In some embodiments, the disclosed compounds can have the structures of Formula II:

Formula II

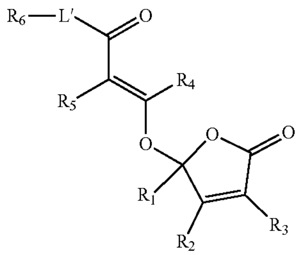

(a) where $R_1$-$R_4$ are as defined above;

(b) where L' is an oxygen atom or a sulfur atom; and (c) where $R_5$ and $R_6$ are independently an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group, where the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

In some embodiments, L' of Formula II is a sulfur atom.

In some embodiments, the disclosed compounds can have the structures of Formula III:

Formula III

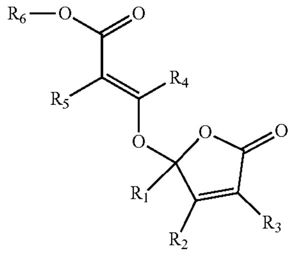

(a) where $R_1$-$R_4$ are independently a hydrogen atom, a halogen atom, an alkyl group, a hydroxyl group, or an amino group;

(b) where $R_5$ and $R_6$ are independently an unsubstituted aryl group, a substituted aryl group, an unsubstituted polyaryl group, a substituted polyaryl group, an unsubstituted alkylaryl group, or a substituted alkylaryl group, where the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group. In some embodiments, the substituents are independently a halogen or an alkyl group, such as a lower alkyl group (i.e. $C_1$-$C_5$ alkyl group).

In some embodiments of Formula III, $R_6$ is an unsubstituted aryl group, a substituted aryl group, an unsubstituted alkylaryl group, a substituted alkylaryl group, an unsubstituted polyaryl group, or a substituted polyaryl group. In some embodiments of Formula III, $R_6$ is an unsubstituted aryl group, a substituted aryl group, or an unsubstituted alkylaryl group. In some embodiments of Formula III, $R_6$ is an unsubstituted aryl group or an unsubstituted alkylaryl group. For example, $R_6$ of Formula III is an unsubstituted alkylaryl group, where the alkyl group of the alkylaryl group is a lower alkyl group (i.e. $C_1$-$C_5$ alkyl group, such as methylaral group or ethylaryl group). In some embodiments of Formula III, $R_6$ is a substituted or unsubstituted polyaryl group having 2-5 aromatic rings. For example, $R_6$ of Formula III can be a substituted or unsubstituted biaryl group.

In some preferred embodiments of Formula III, $R_3$ is a $C_1$-$C_5$ alkyl group or a $C_1$-$C_3$ alkyl group, more preferably, an unsubstituted $C_1$-$C_5$ alkyl group or an unsubstituted $C_1$-$C_3$ alkyl group, such as a methyl group. In some preferred embodiments, $R_1$, $R_2$, and $R_4$ of Formula III are hydrogen. In some particularly preferred embodiments, $R_1$, $R_2$, and $R_4$ of Formula III are hydrogen, and $R_3$ of Formula III is a methyl group.

The substituents on the aryl group can be at the para, meta, or ortho position, or a combination thereof. In some preferred embodiments, the substituent is at the para position on an aryl group.

In some embodiments, the disclosed compounds can have the structures of Formula IV.

Formula IV

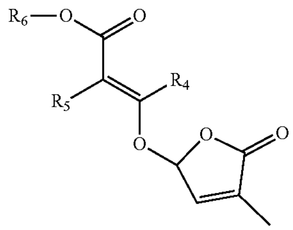

(a) where $R_5$ is an unsubstituted aryl group or a substituted aryl group; and (b) where $R_6$ is an unsubstituted aryl group, a substituted aryl group, an unsubstituted polyaryl group, a substituted polyaryl group, an unsubstituted alkylaryl group, or a substituted alkylaryl group, where the substituents are independently a halogen atom or an alkyl group, such as a lower alkyl group (i.e. $C_1$-$C_5$ alkyl group).

In some embodiments of Formula IV, $R_6$ is an unsubstituted aryl group, a substituted aryl group, an unsubstituted polyaryl, or an unsubstituted alkylaryl group. For example, $R_6$ of Formula IV is an unsubstituted alkylaryl group, where the alkyl group of the alkylaryl group is a lower alkyl group (i.e. $C_1$-$C_5$ alkyl group, such as methylaryl group or ethylaryl group). For example, $R_6$ of Formula IV is a substituted aryl group, where the substituent is a halogen or a lower alkyl group (i.e. $C_1$-$C_5$ alkyl group, such as methylaryl group or ethylaryl group). For example, $R_6$ of Formula IV is an unsubstituted polyaryl group having 2-5 aromatic rings, such as an unsubstituted biaryl.

The substituents on the aryl group can be at the para, meta, or ortho position, or a combination thereof. In some preferred embodiments, the substituent is at the para position on an aryl group.

In some embodiments, in the structures of Formula IV, $R_5$ is an unsubstituted aryl group, and $R_6$ is an unsubstituted polyaryl group (see, for example, MP25 shown below).

In some embodiments, the disclosed compounds can have the structures of Formula V.

Formula V

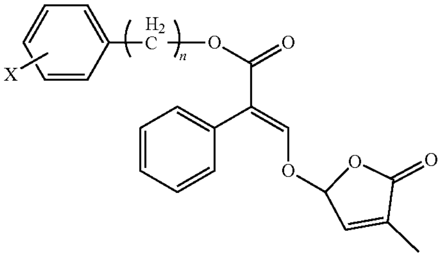

(a) where n is 0 or a positive integer between 1 and 5; and
(b) where X is a hydrogen atom, a halogen atom, or an alkyl group.

In some embodiments, n can be 0, 1, 2, 3, 4, or 5, such as 0, 1, 2, or 3, preferably 0 or 1.

X can be at the para, meta, or ortho position on the aryl group, or a combination thereof. In some preferred embodiments, X is at the para position on an aryl group.

In some embodiments, the disclosed compounds can have the structures of Formula VI.

Formula VI

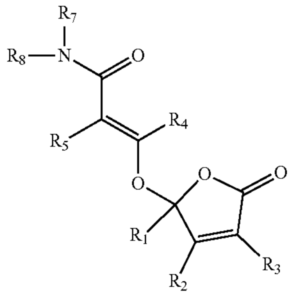

(a) where $R_1$-$R_4$ are as defined above;
(b) where $R_5$ is an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group; and
(c) where $R_7$ and $R_8$ are independently a hydrogen atom, an unsubstituted alkyl group, a substituted alkyl group, an unsubstituted heteroalkyl group, a substituted heteroalkyl group, an unsubstituted alkenyl group, a substituted alkenyl group, an unsubstituted heteroalkenyl group, a substituted heteroalkenyl group, an unsubstituted alkynyl group, a substituted alkynyl group, an unsubstituted heteroalkynyl group, a substituted heteroalkynyl group, an unsubstituted aryl group, a substituted aryl group, an unsubstituted an unsubstituted heteroaryl group, or a substituted heteroaryl group, where the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

In some preferred embodiments of Formula VI, $R_1$-$R_4$, $R_5$, $R_7$ and $R_8$ are as follows:

(a) $R_1$-$R_4$ are independently a hydrogen atom, a halogen atom, an alkyl group, a hydroxyl group, or an amino group;

(b) $R_5$ is an unsubstituted aryl group, a substituted aryl group, an unsubstituted polyaryl group, a substituted polyaryl group, an unsubstituted alkylaryl group, or a substituted alkylaryl group; and (c) $R_7$ and $R_8$ are independently a hydrogen atom, an unsubstituted alkyl group, a substituted alkyl group, an unsubstituted heteroalkyl group, a substituted heteroalkyl group, an unsubstituted aryl group, a substituted aryl group, an unsubstituted heteroaryl group, a substituted heteroaryl group, an unsubstituted alkylaryl group, or a substituted alkylaryl group, where the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

In some preferred embodiments, $R_3$ of Formula VI is a $C_1$-$C_5$ alkyl group or a $C_1$-$C_3$ alkyl group, more preferably, an unsubstituted $C_1$-$C_5$ alkyl group or an unsubstituted $C_1$-$C_3$ alkyl group, such as a methyl group. In some preferred embodiments, $R_1$, $R_2$, and $R_4$ of Formula VI are hydrogen. In some particularly preferred embodiments, $R_1$, $R_2$, and $R_4$ of Formula VI are hydrogen, and $R_3$ of Formula VI is a methyl group. In some embodiments of Formula VI, $R_7$ and $R_8$ are independently a $C_1$-$C_5$ alkyl group or $C_1$-$C_3$ alkyl group. In more preferred embodiments of Formula VI, $R_7$ and $R_8$ are independently an unsubstituted $C_1$-$C_5$ alkyl group or unsubstituted $C_1$-$C_3$ alkyl group, for example, $R_7$ and $R_8$ can be independently a methyl group, an ethyl group, a propyl group, or a butyl group, such as a methyl group.

In some embodiments, the disclosed compounds can have the structures of Formula VII.

Formula VII

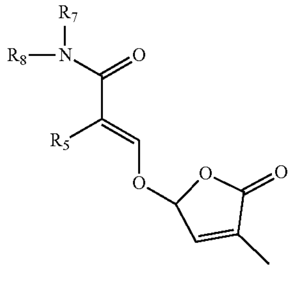

(a) where $R_5$ is an unsubstituted aryl group or a substituted aryl group; and (b) where $R_7$ and $R_8$ are independently a hydrogen atom, an unsubstituted alkyl group, a substituted alkyl group, an unsubstituted aryl group, a substituted aryl group, an unsubstituted alkylaryl group, or a substituted alkylaryl group, where the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

In some embodiments of Formula VII, $R_7$ and $R_8$ are independently a $C_1$-$C_5$ alkyl group or $C_1$-$C_3$ alkyl group. In more preferred embodiments of Formula VII, $R_7$ and $R_8$ are independently an unsubstituted $C_1$-$C_5$ alkyl group or unsubstituted $C_1$-$C_3$ alkyl group, for example, $R_7$ and $R_8$ can be independently a methyl group, an ethyl group, a propyl group, or a butyl group, such as a methyl group.

In some embodiments, the disclosed compounds can have the structures of Formula VIII.

Formula VIII

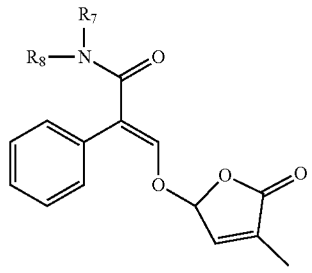

where $R_7$ and $R_8$ are independently a hydrogen atom, an unsubstituted alkyl group, or a substituted alkyl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

In some preferred embodiments of Formula VIII, $R_7$ and $R_8$ are independently a $C_1$-$C_5$ alkyl group or $C_1$-$C_3$ alkyl group. In more preferred embodiments of Formula VIII, $R_7$ and $R_8$ are independently an unsubstituted $C_1$-$C_5$ alkyl group or unsubstituted $C_1$-$C_3$ alkyl group, for example, $R_7$ and $R_8$ can be independently a methyl group, an ethyl group, a propyl group, or a butyl group, such as a methyl group.

Generally, the alkyl group can be linear, branched, or cyclic. An alkyl can be a linear $C_1$-$C_{30}$ alkyl, a branched $C_4$-$C_{30}$ alkyl, a cyclic $C_3$-$C_{30}$ alkyl, a linear $C_1$-$C_{30}$ alkyl or a branched $C_4$-$C_{30}$ alkyl, a linear $C_1$-$C_{30}$ alkyl or a cyclic $C_3$-$C_{30}$ alkyl, a branched $C_4$-$C_{30}$ alkyl or a cyclic $C_3$-$C_{30}$ alkyl. Optionally, alkyl groups have up to 20 carbon atoms. An alkyl can be a linear $C_1$-$C_{20}$ alkyl, a branched $C_4$-$C_{20}$ alkyl, a cyclic $C_3$-$C_{20}$ alkyl, a linear $C_1$-$C_{20}$ alkyl or a branched $C_4$-$C_{20}$ alkyl, a branched $C_4$-$C_{20}$ alkyl or a cyclic $C_3$-$C_{20}$ alkyl, a linear $C_1$-$C_{20}$ alkyl or a cyclic $C_3$-$C_{20}$ alkyl. Optionally, alkyl groups have up to 10 carbon atoms. An alkyl can be a linear $C_1$-$C_{10}$ alkyl, a branched $C_4$-$C_{10}$ alkyl, a cyclic $C_3$-$C_{10}$ alkyl, a linear $C_1$-$C_{10}$ alkyl or a branched $C_4$-$C_{10}$ alkyl, a branched $C_4$-$C_{10}$ alkyl or a cyclic $C_3$-$C_{10}$ alkyl, a linear $C_1$-$C_{10}$ alkyl or a cyclic $C_3$-$C_{10}$ alkyl. Optionally, alkyl groups have up to 6 carbon atoms. An alkyl can be a linear $C_1$-$C_6$ alkyl, a branched $C_4$-$C_6$ alkyl, a cyclic $C_3$-$C_6$ alkyl, a linear $C_1$-$C_6$ alkyl or a branched $C_4$-$C_6$ alkyl, a branched $C_4$-$C_6$ alkyl or a cyclic $C_3$-$C_6$ alkyl, or a linear $C_1$-$C_6$ alkyl or a cyclic $C_3$-$C_6$ alkyl. Optionally, alkyl groups have up to four carbons. An alkyl can be a linear $C_1$-$C_4$ alkyl, cyclic $C_3$-$C_4$ alkyl, a linear $C_1$-$C_4$ alkyl or a cyclic $C_3$-$C_4$ alkyl. Preferably, the alkyl group is unsubstituted alkyl group. Preferably, the alkyl group is a linear $C_1$-$C_5$, $C_1$-$C_4$, $C_1$-$C_3$, $C_1$-$C_2$ alkyl group, such as methyl group.

Generally, the heteroalkyl group can be linear, branched, or cyclic. A heteroalkyl can be a linear $C_1$-$C_{30}$ heteroalkyl, a branched $C_3$-$C_{30}$ heteroalkyl, a cyclic $C_2$-$C_{30}$ heteroalkyl, a linear $C_1$-$C_{30}$ heteroalkyl or a branched $C_3$-$C_{30}$ heteroalkyl, a linear $C_1$-$C_{30}$ heteroalkyl or a cyclic $C_2$-$C_{30}$ heteroalkyl, a branched $C_3$-$C_{30}$ heteroalkyl or a cyclic $C_2$-$C_{30}$ heteroalkyl. Optionally, heteroalkyl groups have up to 20 carbon atoms. A heteroalkyl can be a linear $C_1$-$C_{20}$ heteroalkyl, a branched $C_3$-$C_{20}$ heteroalkyl, a cyclic $C_2$-$C_{20}$ heteroalkyl, a linear $C_1$-$C_{20}$ heteroalkyl or a branched $C_3$-$C_{20}$ heteroalkyl, a branched $C_3$-$C_{20}$ heteroalkyl or a cyclic $C_2$-$C_{20}$ heteroalkyl, or a linear $C_1$-$C_{20}$ heteroalkyl or a cyclic $C_2$-$C_{20}$ heteroalkyl. Optionally, heteroalkyl groups have up to 10 carbon atoms. A heteroalkyl can be a linear $C_1$-$C_{10}$ heteroalkyl, a branched $C_3$-$C_{10}$ heteroalkyl, a cyclic $C_2$-$C_{10}$ heteroalkyl, a linear $C_1$-$C_{10}$ heteroalkyl or a branched $C_3$-$C_{10}$ heteroalkyl, a branched $C_3$-$C_{10}$ heteroalkyl or a cyclic $C_2$-$C_{10}$ heteroalkyl, or a linear $C_1$-$C_{10}$ heteroalkyl or a cyclic $C_2$-$C_{10}$ heteroalkyl. Optionally, heteroalkyl groups have up to 6 carbon atoms. A heteroalkyl can be a linear $C_1$-$C_6$ heteroalkyl, a branched $C_3$-$C_6$ heteroalkyl, a cyclic $C_2$-$C_6$ heteroalkyl, a linear $C_1$-$C_6$ heteroalkyl or a branched $C_3$-$C_6$ heteroalkyl, a branched $C_3$-$C_6$ heteroalkyl or a cyclic $C_2$-$C_6$ heteroalkyl, or a linear $C_1$-$C_6$ heteroalkyl or a cyclic $C_2$-$C_6$ heteroalkyl. Optionally, heteroalkyl groups have up to four carbons. A heteroalkyl can be a linear $C_1$-$C_4$ heteroalkyl, a branched $C_3$-$C_4$ heteroalkyl, a cyclic $C_2$-$C_4$ heteroalkyl, a linear $C_1$-$C_4$ heteroalkyl or a branched $C_3$-$C_4$ heteroalkyl, a branched $C_3$-$C_4$ heteroalkyl or a cyclic $C_2$-$C_4$ heteroalkyl, or a linear $C_1$-$C_4$ heteroalkyl or a cyclic $C_2$-$C_4$ heteroalkyl.

Generally, the alkenyl group can be linear, branched, or cyclic. An alkenyl can be a linear $C_2$-$C_{30}$ alkenyl, a branched $C_4$-$C_{30}$ alkenyl, a cyclic $C_3$-$C_{30}$ alkenyl, a linear $C_2$-$C_{30}$ alkenyl or a branched $C_4$-$C_{30}$ alkenyl, a linear $C_2$-$C_{30}$ alkenyl or a cyclic $C_3$-$C_{30}$ alkenyl, a branched $C_4$-$C_{30}$ alkenyl or a cyclic $C_3$-$C_{30}$ alkenyl. Optionally, alkenyl groups have up to 20 carbon atoms. An alkenyl can be a linear $C_2$-$C_{20}$ alkenyl, a branched $C_4$-$C_{20}$ alkenyl, a cyclic $C_3$-$C_{20}$ alkenyl, a linear $C_2$-$C_{20}$ alkenyl or a branched $C_4$-$C_{20}$ alkenyl, a linear $C_2$-$C_{20}$ alkenyl or a cyclic $C_3$-$C_{20}$ alkenyl, a branched $C_4$-$C_{20}$ alkenyl or a cyclic $C_3$-$C_{20}$ alkenyl. Optionally, alkenyl groups have two to 10 carbon atoms. An alkenyl can be a linear $C_2$-$C_{10}$ alkenyl, a branched $C_4$-$C_{10}$ alkenyl, a cyclic $C_3$-$C_{10}$ alkenyl, a linear $C_2$-$C_{10}$ alkenyl or a branched $C_4$-$C_{10}$ alkenyl, a linear $C_2$-$C_{10}$ alkenyl or a cyclic $C_3$-$C_{10}$ alkenyl, a branched $C_4$-$C_{10}$ alkenyl or a cyclic $C_3$-$C_{10}$ alkenyl. Optionally, alkenyl groups have two to 6 carbon atoms. An alkenyl can be a linear $C_2$-$C_6$ alkenyl, a branched $C_4$-$C_6$ alkenyl, a cyclic $C_3$-$C_6$ alkenyl, a linear $C_2$-$C_6$ alkenyl or a branched $C_4$-$C_6$ alkenyl, a linear $C_2$-$C_6$ alkenyl or a cyclic $C_3$-$C_6$ alkenyl, a branched $C_4$-$C_6$ alkenyl or a cyclic $C_3$-$C_6$ alkenyl. Optionally, alkenyl groups have two to four carbons. An alkenyl can be a linear $C_2$-$C_4$ alkenyl, a cyclic $C_3$-$C_4$ alkenyl, a linear $C_2$-$C_4$ alkenyl or a cyclic $C_3$-$C_4$ alkenyl.

Generally, the heteroalkenyl group can be linear, branched, or cyclic. A heteroalkenyl can be a linear $C_2$-$C_{30}$ heteroalkenyl, a branched $C_3$-$C_{30}$ heteroalkenyl, a cyclic $C_2$-$C_{30}$ heteroalkenyl, a linear $C_2$-$C_{30}$ heteroalkenyl or a branched $C_3$-$C_{30}$ heteroalkenyl, a linear $C_2$-$C_{30}$ heteroalkenyl or a cyclic $C_2$-$C_{30}$ heteroalkenyl, a branched $C_3$-$C_{30}$ heteroalkenyl or a cyclic $C_2$-$C_{30}$ heteroalkenyl. Optionally, heteroalkenyl groups have up to 20 carbon atoms. A heteroalkenyl can be a linear $C_2$-$C_{20}$ heteroalkenyl, a branched $C_3$-$C_{20}$ heteroalkenyl, a cyclic $C_2$-$C_{20}$ heteroalkenyl, a linear $C_2$-$C_{20}$ heteroalkenyl or a branched $C_3$-$C_{20}$ heteroalkenyl, a linear $C_2$-$C_{20}$ heteroalkenyl or a cyclic $C_2$-$C_{20}$ heteroalkenyl, a branched $C_3$-$C_{20}$ heteroalkenyl or a cyclic $C_2$-$C_{20}$ heteroalkenyl. Optionally, heteroalkenyl groups have up to 10 carbon atoms. A heteroalkenyl can be a linear $C_2$-$C_{10}$ heteroalkenyl, a branched $C_3$-$C_{10}$ heteroalkenyl, a cyclic $C_2$-$C_{10}$ heteroalkenyl, a linear $C_2$-$C_{10}$ heteroalkenyl or a branched $C_3$-$C_{10}$ heteroalkenyl, a linear $C_2$-$C_{10}$ heteroalkenyl or a cyclic $C_2$-$C_{10}$ heteroalkenyl, a branched $C_3$-$C_{10}$ heteroalkenyl or a cyclic $C_2$-$C_{10}$ heteroalkenyl. Optionally, heteroalkenyl groups have two to 6 carbon atoms. A heteroalkenyl can be a linear $C_2$-$C_6$ heteroalkenyl, a branched $C_3$-$C_6$ heteroalkenyl, a cyclic $C_2$-$C_6$ heteroalkenyl, a linear $C_2$-$C_6$ heteroalkenyl or a branched $C_3$-$C_6$ heteroalkenyl, a linear $C_2$-$C_6$ heteroalkenyl or a cyclic $C_2$-$C_6$ heteroalkenyl, a branched $C_3$-$C_6$ heteroalkenyl or a cyclic $C_2$-$C_6$ heteroalkenyl. Optionally, heteroalkenyl groups have two to four carbons. A heteroalkenyl can be a linear $C_2$-$C_4$ heteroalkenyl, a branched $C_3$-$C_4$ heteroalkenyl, a cyclic $C_2$-$C_4$ heteroalkenyl, a linear $C_2$-$C_4$ heteroalkenyl or a branched $C_3$-$C_4$ heteroalkenyl, a linear $C_2$-$C_4$ heteroalkenyl or a cyclic $C_2$-$C_4$ heteroalkenyl, a branched $C_3$-$C_4$ heteroalkenyl or a cyclic $C_2$-$C_4$ heteroalkenyl.

Generally, the alkynyl group can be linear, branched, or cyclic. An alkynyl can be a linear $C_2$-$C_{30}$ alkynyl, a branched $C_4$-$C_{30}$ alkynyl, a cyclic $C_3$-$C_{30}$ alkynyl, a linear $C_2$-$C_{30}$ alkynyl or a branched $C_4$-$C_{30}$ alkynyl, a linear $C_2$-$C_{30}$ alkynyl or a cyclic $C_3$-$C_{30}$ alkynyl, a branched $C_4$-$C_{30}$ alkynyl or a cyclic $C_3$-$C_{30}$ alkynyl. Optionally, alkynyl groups have up to 20 carbon atoms. An alkynyl can be a linear $C_2$-$C_{20}$ alkynyl, a branched $C_4$-$C_{20}$ alkynyl, a cyclic $C_3$-$C_{20}$ alkynyl, a linear $C_2$-$C_{20}$ alkynyl or a branched $C_4$-$C_{20}$ alkynyl, a branched $C_4$-$C_{20}$ alkynyl or a cyclic $C_3$-$C_{20}$ alkynyl. Optionally, alkynyl groups have up to 10 carbon atoms. An alkynyl can be a linear $C_2$-$C_{10}$ alkynyl, a branched $C_4$-$C_{10}$ alkynyl, a cyclic $C_3$-$C_{10}$ alkynyl, a linear $C_2$-$C_{20}$ alkynyl or a branched $C_4$-$C_{10}$ alkynyl, a branched $C_4$-$C_{20}$ alkynyl or a cyclic $C_3$-$C_{10}$ alkynyl, a linear $C_2$-$C_{20}$ alkynyl or a cyclic $C_3$-$C_{20}$ alkynyl. Optionally, alkynyl groups have up to 6 carbon atoms. An alkynyl can be a linear $C_2$-$C_6$ alkynyl, a branched $C_4$-$C_6$ alkynyl, a cyclic $C_3$-$C_6$ alkynyl, a linear $C_2$-$C_6$ alkynyl or a branched $C_4$-$C_6$ alkynyl, a branched $C_4$-$C_6$ alkynyl or a cyclic $C_3$-$C_6$ alkynyl, a linear $C_2$-$C_6$ alkynyl or a cyclic $C_3$-$C_6$ alkynyl. Optionally, alkynyl groups have up to four carbons. An alkynyl can be a linear $C_2$-$C_4$ alkynyl, a cyclic $C_3$-$C_4$ alkynyl, a linear $C_2$-$C_4$ alkynyl or a cyclic $C_3$-$C_4$ alkynyl.

Generally, the heteroalkynyl group can be linear, branched, or cyclic. A heteroalkynyl can be a linear $C_2$-$C_{30}$ heteroalkynyl, a branched $C_3$-$C_{30}$ heteroalkynyl, a cyclic $C_2$-$C_{30}$ heteroalkynyl, a linear $C_2$-$C_{30}$ heteroalkynyl or a branched $C_3$-$C_{30}$ heteroalkynyl, a linear $C_2$-$C_{30}$ heteroalkynyl or a cyclic $C_2$-$C_{30}$ heteroalkynyl, a branched $C_3$-$C_{30}$ heteroalkynyl or a cyclic $C_2$-$C_{30}$ heteroalkynyl. Optionally, heteroalkynyl groups have up to 20 carbon atoms. A heteroalkynyl can be a linear $C_2$-$C_{20}$ heteroalkynyl, a branched $C_3$-$C_{20}$ heteroalkynyl, a cyclic $C_2$-$C_{20}$ heteroalkynyl, a linear $C_2$-$C_{20}$ heteroalkynyl or a branched $C_3$-$C_{20}$ heteroalkynyl, a branched $C_3$-$C_{20}$ heteroalkynyl or a cyclic $C_2$-$C_{20}$ heteroalkynyl, a linear $C_2$-$C_{20}$ heteroalkynyl or a cyclic $C_2$-$C_{20}$ heteroalkynyl. Optionally, heteroalkynyl groups have up to 10 carbon atoms. A heteroalkynyl can be a linear $C_2$-$C_{10}$ heteroalkynyl, a branched $C_3$-$C_{10}$ heteroalkynyl, a cyclic $C_2$-$C_{10}$ heteroalkynyl, a linear $C_2$-$C_{10}$ heteroalkynyl or a branched $C_3$-$C_{10}$ heteroalkynyl, a branched $C_3$-$C_{10}$ heteroalkynyl or a cyclic $C_2$-$C_{10}$ heteroalkynyl, a linear $C_2$-$C_{10}$ heteroalkynyl or a cyclic $C_2$-$C_{10}$ heteroalkynyl. Optionally, heteroalkynyl groups have two to 6 carbon atoms. A heteroalkynyl can be a linear $C_2$-$C_6$ heteroalkynyl, a branched $C_3$-$C_6$ heteroalkynyl, a cyclic $C_2$-$C_6$ heteroalkynyl, a linear $C_2$-$C_6$ heteroalkynyl or a branched $C_3$-$C_6$ heteroalkynyl, a branched $C_3$-$C_6$ heteroalkynyl or a cyclic $C_2$-$C_6$ heteroalkynyl, a linear $C_2$-$C_6$ heteroalkynyl or a cyclic $C_2$-$C_6$ heteroalkynyl. Optionally, heteroalkynyl groups have up to four carbons. A heteroalkynyl can be a linear $C_2$-$C_4$ heteroalkynyl, a branched $C_3$-$C_4$ heteroalkynyl, a cyclic $C_2$-$C_4$ heteroalkynyl, a linear $C_2$-$C_4$ heteroalkynyl or a branched $C_3$-$C_4$ heteroalkynyl, a branched $C_3$-$C_4$ heteroalkynyl or a cyclic $C_2$-$C_4$ heteroalkynyl, a linear $C_2$-$C_4$ heteroalkynyl or a cyclic $C_2$-$C_4$ heteroalkynyl.

Generally, the aryl group can have six to 50 carbon atoms. An aryl can be a branched $C_6$-$C_{50}$ aryl, a monocyclic $C_6$-$C_{50}$ aryl, a polycyclic $C_6$-$C_{50}$ aryl, a branched polycyclic $C_6$-$C_{50}$ aryl, a fused polycyclic $C_6$-$C_{50}$ aryl, or a branched fused polycyclic $C_6$-$C_{50}$ aryl. Optionally, aryl groups have six to 30 carbon atoms, i.e., $C_6$-$C_{30}$ aryl. A $C_6$-$C_{30}$ aryl can be a branched $C_6$-$C_{30}$ aryl, a monocyclic $C_6$-$C_{30}$ aryl, a polycyclic $C_6$-$C_{30}$ aryl, a branched polycyclic $C_6$-$C_{30}$ aryl, a fused polycyclic $C_6$-$C_{30}$ aryl, or a branched fused polycyclic $C_6$-$C_{30}$ aryl. Optionally, aryl groups have six to 20 carbon atoms, i.e., $C_6$-$C_{20}$ aryl. A $C_6$-$C_{20}$ aryl can be a branched $C_6$-$C_{20}$ aryl, a monocyclic $C_6$-$C_{20}$ aryl, a polycyclic $C_6$-$C_{20}$ aryl, a branched polycyclic $C_6$-$C_{20}$ aryl, a fused polycyclic $C_6$-$C_{20}$ aryl, or a branched fused polycyclic $C_6$-$C_{20}$ aryl. Optionally, aryl groups have six to twelve carbon atoms, i.e., $C_6$-$C_{12}$ aryl. A $C_6$-$C_{12}$ aryl can be a branched $C_6$-$C_{12}$ aryl, a monocyclic $C_6$-$C_{12}$ aryl, a polycyclic $C_6$-$C_{12}$ aryl, a branched polycyclic $C_6$-$C_{12}$ aryl, a fused polycyclic $C_6$-$C_{12}$ aryl, or a branched fused polycyclic $C_6$-$C_{12}$ aryl. Optionally, $C_6$-$C_{12}$ aryl groups have six to eleven carbon atoms, i.e., $C_6$-$C_{11}$ aryl. A $C_6$-$C_{11}$ aryl can be a branched $C_6$-$C_{11}$ aryl, a monocyclic $C_6$-$C_{11}$ aryl, a polycyclic $C_6$-$C_{11}$ aryl, a branched polycyclic $C_6$-$C_{11}$ aryl, a fused polycyclic $C_6$-$C_{11}$ aryl, or a branched fused polycyclic $C_6$-$C_{11}$ aryl. Optionally, $C_6$-$C_{12}$ aryl groups have six to nine carbon atoms, i.e., $C_6$-$C_9$ aryl. A $C_6$-$C_9$ aryl can be a branched $C_6$-$C_9$ aryl, a monocyclic $C_6$-$C_9$ aryl, a polycyclic $C_6$-$C_9$ aryl, a branched polycyclic $C_6$-$C_9$ aryl, a fused polycyclic $C_6$-$C_9$ aryl, or a branched fused polycyclic $C_6$-$C_9$ aryl. Optionally, $C_6$-$C_{12}$ aryl groups have six carbon atoms, i.e., $C_6$ aryl. A $C_6$ aryl can be a branched $C_6$ aryl or a monocyclic $C_6$ aryl.

Generally, the heteroaryl group can have three to 50 carbon atoms, i.e., $C_3$-$C_{50}$ heteroaryl. A $C_3$-$C_{50}$ heteroaryl can be a branched $C_3$-$C_{50}$ heteroaryl, a monocyclic $C_3$-$C_{50}$ heteroaryl, a polycyclic $C_3$-$C_{50}$ heteroaryl, a branched polycyclic $C_3$-$C_{50}$ heteroaryl, a fused polycyclic $C_3$-$C_{50}$ heteroaryl, or a branched fused polycyclic $C_3$-$C_{50}$ heteroaryl. Optionally, heteroaryl groups have six to 30 carbon atoms, i.e., $C_6$-$C_{30}$ heteroaryl. A $C_6$-$C_{30}$ heteroaryl can be a branched $C_6$-$C_{30}$ heteroaryl, a monocyclic $C_6$-$C_{30}$ heteroaryl, a polycyclic $C_6$-$C_{30}$ heteroaryl, a branched polycyclic $C_6$-$C_{30}$ heteroaryl, a fused polycyclic $C_6$-$C_{30}$ heteroaryl, or a branched fused polycyclic $C_6$-$C_{30}$ heteroaryl. Optionally, heteroaryl groups have six to 20 carbon atoms, i.e., $C_6$-$C_{20}$ heteroaryl. A $C_6$-$C_{20}$ heteroaryl can be a branched $C_6$-$C_{20}$ heteroaryl, a monocyclic $C_6$-$C_{20}$ heteroaryl, a polycyclic $C_6$-Cao heteroaryl, a branched polycyclic $C_6$-$C_{20}$ heteroaryl, a fused polycyclic $C_6$-$C_{20}$ heteroaryl, or a branched fused polycyclic $C_6$-$C_{20}$ heteroaryl. Optionally, heteroaryl groups have six to twelve carbon atoms, i.e., $C_6$-$C_{12}$ heteroaryl. A $C_6$-$C_{12}$ heteroaryl can be a branched $C_6$-$C_{12}$ heteroaryl, a monocyclic $C_6$-$C_{12}$ heteroaryl, a polycyclic $C_6$-$C_{12}$ heteroaryl, a branched polycyclic $C_6$-$C_{12}$ heteroaryl, a fused polycyclic $C_6$-$C_{12}$ heteroaryl, or a branched fused polycyclic $C_6$-$C_{12}$ heteroaryl. Optionally, $C_6$-$C_{12}$ heteroaryl groups have six to eleven carbon atoms, i.e., $C_6$-$C_{11}$ heteroaryl. A $C_6$-$C_{11}$ heteroaryl can be a branched $C_6$-$C_{11}$ heteroaryl, a monocyclic $C_6$-$C_{11}$ heteroaryl, a polycyclic $C_6$-$C_{11}$ heteroaryl, a branched polycyclic $C_6$-$C_{11}$ heteroaryl, a fused polycyclic $C_6$-$C_{11}$ heteroaryl, or a branched fused polycyclic $C_6$-$C_{11}$ heteroaryl. Optionally, $C_6$-$C_{12}$ heteroaryl groups have six to nine carbon atoms, i.e., $C_6$-$C_9$ heteroaryl. A $C_6$-$C_9$ heteroaryl can be a branched $C_6$-$C_9$ heteroaryl, a monocyclic $C_6$-$C_9$ heteroaryl, a polycyclic $C_6$-$C_9$ heteroaryl, a branched polycyclic $C_6$-$C_9$ heteroaryl, a fused polycyclic $C_6$-$C_9$ heteroaryl, or a branched fused polycyclic $C_6$-$C_9$ heteroaryl. Optionally, $C_6$-$C_{12}$ heteroaryl groups have six carbon atoms, i.e., $C_6$ heteroaryl. A $C_6$ heteroaryl can be a branched $C_6$ heteroaryl, a monocyclic $C_6$ heteroaryl, a polycyclic $C_6$ heteroaryl, a branched polycyclic $C_6$ heteroaryl, a fused polycyclic $C_6$ heteroaryl, or a branched fused polycyclic $C_6$ heteroaryl.

Exemplary and preferred compounds having the structures of Formulas I-VIII include compounds MP16-MP18 and MP21-MP25, the structures of which are shown below.

MP16

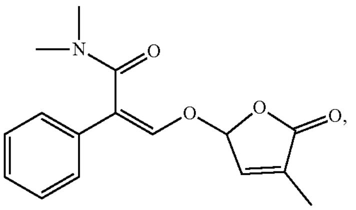

MP17

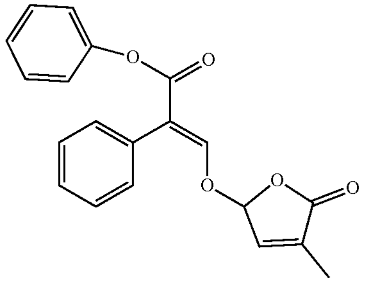

MP18

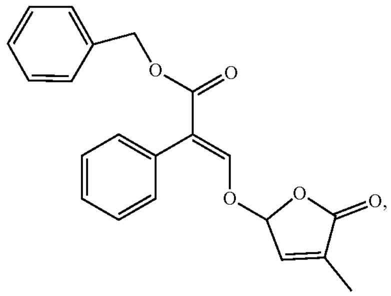

-continued

MP21

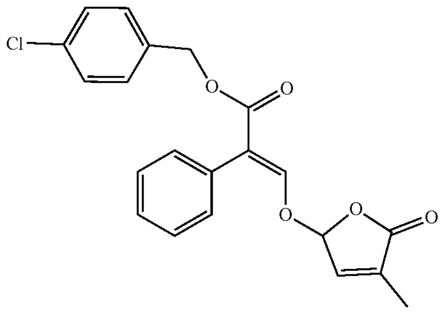

MP22

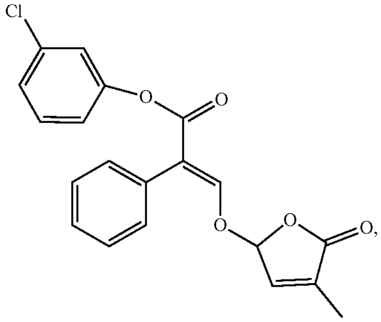
,

MP23

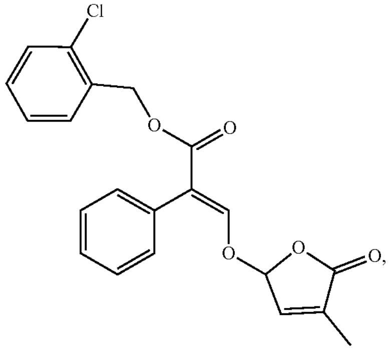
,

MP24

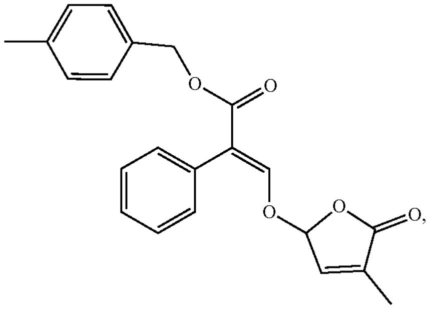
,

-continued

MP25

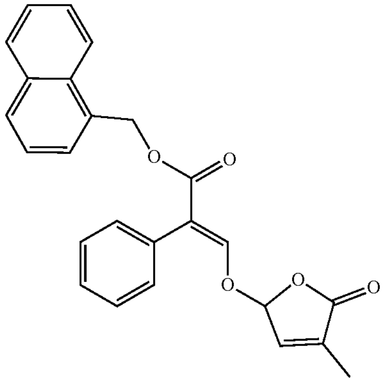

In some embodiments, the salts of Formulas I-VIII can be prepared by treating the free acid form of the compounds with an appropriate amount of a base. Exemplary bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like.

B. Formulations

The compounds disclosed herein or salts thereof can be used in unmodified form. Alternatively, the compounds can be formulated into formulations in combination with one or more formulation excipients, in a suitable carrier.

The formulations can be in various forms, as described below.

Formulation excipients are generally materials that can be used to deliver active ingredients, such as the compounds described herein, to a plant (e.g., seedling or mature plant), a plant part (e.g., a seed, leaf, or leaf segment), or a growing site of a plant (e.g., soil or growth medium), without having an adverse effect on plant growth, growth medium structure, soil drainage, or the like.

Generally, the one or more compounds or salts thereof in the one or more formulations are in an effective amount to regulate plant growth, and/or induce parasitic germination. For example, the one or more compounds or salts thereof in the one or more formulations are in an effective amount to inhibit tillering of the plant and/or trigger dark-induced leaf senescence. In some embodiments, the one or more compounds or salts thereof in the one or more formulations are in an effective amount to inhibit tillering of the plant and/or trigger dark-induced leaf senescence, as well as inducing seed germination of one or more parasitic plants.

In some embodiments, the one or more compounds or salts thereof in the one or more formulations are in an effective amount to cause stunted growth and/or trigger senescence in the plant or plant part (e.g. seedlings or seeds of the plant), leading to reduced biomass and/or plant height.

The formulations may contain from about 0.1% to about 95% of the compounds or salts thereof by weight, such as between about 5% and about 95%, between about 0.1% and about 90% by weight, between about 1% and about 80% by weight, between about 1% and about 60% by weight, between about 1% and about 50% by weight, between about 1% and about 40% by weight, between about 1% and about 30% by weight, between about 1% and about 20% by weight, or between about 1% and about 10% by weight.

In embodiments where the formulation is a liquid, the compounds or salts thereof can have a concentration between about 0.1 μM and about 10 M, between about 1 μM and about 1 M, between about 1 μM and about 100 mM, or between about 1 μM and about 10 mM, such as up to about 1 M, up to about 500 mM, up to about 100 mM, at least 1 mM, at least 10 mM, or at least 50 mM. In some preferred embodiments, the compounds or salts thereof in the formulation have a concentration between about 0.1 μM and about 100 μM, between about 0.1 μM and about 10 μM, between about 1 μM and about 10 μM, or between about 1 μM and about 5 μM, such as about 2.5 μM or about 3 μM.

In embodiments where the formulation is diluted prior to use, after dilution, the compounds or salts thereof can have a concentration between about 0.1 μM and about 1 mM, between about 0.1 μM and about 10 μM, or between about 1 μM and about 10 μM, such as about 2.5 μM or about 3 μM.

The specific amount of compounds in the formulation depends on the formulation form, application equipment, and nature of the plants to be treated.

Optionally, the formulations can include one or more additional plant growth regulators that are different from the disclosed compounds, for example, auxins, cytokinins (CKs), gibberellins (GBs), abscisic acid (ABA), ethylene, brassinosteroids, salicylic acid, jasmonates, plant peptide hormones, polyamines, nitric oxide (NO), strigolactones, karrikins, zaxinone (Wang, et al., *Nature Communication,* 10:810 (2019); Wang, et al., *Molecular Plant,* 13:1654-1661 (2020)), mimics of zaxinone, or a combination thereof. Additionally or alternatively, the formulations can include one or more inhibitors of the biosynthesis of above-described plant growth regulators and/or one or more receptors of the above-descried plant growth regulators. For example, the formulations can include one or more of the disclosed compounds, and optionally one or more additional plant growth regulators that are different from the disclosed compounds, one or more inhibitors of the biosynthesis of the plant growth regulators that are different from the disclosed compounds, and/or one or more receptors of the plant growth regulators that are different from the disclosed compounds. The relative concentration or weight amount of the disclosed compounds and the additional growth regulators, the inhibitors of the biosynthesis of the growth regulators, and/or the receptors of the growth regulators can be adjusted to achieve effective amounts and synergistic effects.

Optionally, the formulation can include one or more penetration enhancers to facilitate delivery of the disclosed compounds. Penetration enhancers can accelerate the uptake of agrochemical through the cuticle of a plant into the plant, thus increase the rate of uptake and/or the amount of agrochemical absorbed into the plant. Penetration enhancers are known, see, for example, US 2010/0048516 by Bauer et al., discloses tributoxyethyl phosphate (TBEP); Various classes of substances are already known as penetration enhancers (cf. for example WO 2005/104844 A). DE 3513889 A1 generally discusses penetration enhancers as an "activator" for biocides and EP 579052 A2 describes compounds selected from the group consisting of alkyl phosphates, such as tributyl phosphate and tripropyl phosphate, as penetration enhancers Alternatively, the additional plant growth regulator, and/or penetration enhancers can be separate from the formulation and applied concurrently or sequentially with the formulation to a plant, plant part, or growing site of plant.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

1. Formulation Excipients and Carriers

Suitable formulation excipients, such as carriers and surface active agents, are known in the art and are described below. The carriers can be any carriers, including, but not limited to, solid carriers and liquid carriers.

Optionally, more than one suitable formulation excipient may be formulated together and/or mixed separately.

Formulating formulations containing one or more active ingredients, such as compounds disclosed herein, are known in the art.

a. Solid Carriers

Suitable solid carriers include, but are not limited to, plant powders (e.g., soybean flour, tobacco flour, wheat flour, wood flour, walnut shell four, cotton seed hulls, and the like), mineral powders (e.g., clays such as attapulgite clay, kaolin clay, Fubasami clay, pyrophyllite clay, bentonite and acid clay, talcs such as talc powder and agalmatolite powder, silicas such as diatomaceous earth and mica powder, pumice, fuller's earth, diatomaxeous earth, and the like), synthetic hydrated silicon oxide, alumina, talc, kieselguhr, chalk, titanium dioxide, ceramic, other inorganic minerals (e.g., sericite, quartz, sulfur, active carbon, calcium carbonate, hydrated silica, lime, and the like), lignin, and a combination thereof.

b. Liquid Carriers

Suitable liquid carriers include, but are not limited to, water, alcohols (e.g., methyl alcohol, ethyl alcohol, n-propyl alcohol, isopropyl alcohol, butyl alcohol, hexyl alcohol, benzyl alcohol, ethylene glycol, propylene glycol, phenoxyethanol), buffers (e.g. buffered phosphate saline, MES buffer, etc.), ketones (e.g., acetone, methyl ethyl ketone, methyl isobutyl ketone, cyclohexanone), ethers (e.g., diisopropyl ether, 1,4-dioxane, tetrahydrofuran, ethylene glycol monomethyl ether, ethylene glycol dimethyl ether, diethylene glycol monomethyl ether, propylene glycol monomethyl ether, dipropylene glycol monomethyl ether, 3-methoxy-3-methyl-1-butanol), aliphatic hydrocarbons (e.g., hexane, cyclohexane, kerosene, lamp oil, fuel oil, machine oil and so on), aromatic hydrocarbons (e.g., toluene, xylene, ethylbenzene, dodecylbenzene, phenylxylylethane, solvent naphtha, methylnaphthalene), halogenated hydrocarbons (e.g., dichloromethane, trichloroethane, chloroform, carbon tetrachloride), acid amides (e.g., N,N-dimethylformamide, N,N-dimethylacetamide, N-methylpyrrolidone, N-octylpyrrolidone), esters (e.g., butyl lactate, ethyl acetate, butyl acetate, isopropyl myristate, ethyl oleate, diisopropyl adipate, diisobutyl adipate, propylene glycol monomethyl ether acetate, fatty acid glycerin ester, Y-butyrolactone), nitriles (e.g., acetonitrile, isobutyronitrile, propionitrile), carbonates (e.g., propylene carbonate and so on), and vegetable oils (e.g., soybean oil, olive oil, linseed oil, coconut oil, palm oil, peanut oil, malt oil, almond oil, sesame oil, mineral oil, rosmarinic oil, geranium oil, rapeseed oil, cotton seed oil, corn oil, safflower oil, orange oil).

Water is generally the carrier of choice for the dilution of concentrates.

In some embodiments, the liquid carrier is water, ethanol, buffer, or a combination thereof. The buffer is typically in a pH range from about 5.5 to about 7.4, such as 6.5 or 7.3. Preferably, the liquid carrier is water.

c. Surface-Active Agents

Surface-active agents may be mixed with any solid and liquid carriers described above to form the formulations. Optionally, one or more surface-active agents are included in formulations designed to be diluted with a carrier, such as water or buffer, before application.

Surface-active agents can be anionic, cationic, non-ionic or polymeric.

Optionally, surface-active agents are employed as emulsifying agents, wetting agents, and/or suspending agents.

Suitable surface-active agents include, but are not limited to, salts of alkyl sulfates, such as Atlas G-1086 (product name, manufactured by Croda industrial chemicals), diethanolammonium lauryl sulphate; alkylarylsulfonate salts, such as calcium dodecylbenzenesulfonate; alkylphenol-alkylene oxide addition products, such as nonylpheno 1-C. sub. 18 ethoxylate; alcohol-alkylene oxide addition products, such as tridecyl alcoho 1-C. sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

In some embodiments, the surface-active agent is Atlas G-1086.

d. Other Formulation Excipients

Other excipients commonly utilized in agricultural compositions can be included in the disclosed formulations and they include, but are not limited to, crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like. Casein, gelatin, saccharides (e.g., starch, Xanthan gum, gum arabic, cellulose derivatives, and alginic acid), lignin derivatives, bentonite, synthetic water-soluble polymers (e.g., polyvinyl alcohol, polyvinyl pyrrolidone, polyacrylic acids), PAP (acidic isopropyl phosphate), BHT (2,6-di-tert-butyl-4-methylphenol), and BHA (mixture of 2-tert-butyl-4-methoxyphenol and 3-tert-butyl-4-methoxyphenol) can also be used.

2. Forms of Formulations

The formulations can be in various physical forms, for example, dusting powders, aerosols, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oil dispersions, suspoemulsions capsule suspensions, emulsifiable granules, soluble liquids, water-soluble concentrates (with water or a water miscible organic solvent as carrier), or impregnated polymer films The above described formulations can be applied directly or diluted prior to use. Diluted formulation can be prepared, for example, with water. Exemplary formulations are disclosed herein.

Wettable powders are generally in the form of finely divided particles which disperse readily in water or other liquid carriers. The particles contain the compounds retained in a solid matrix.

Suitable solid matrices include, but are not limited to, fuller's earth, kaolin clays, silicas and other readily wet organic or inorganic solids.

Wettable powders normally contain a small amount of surface-active agents as emulsifying agents, wetting agents, and/or suspending agents.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents.

Emulsifiable concentrates are typically dispersed in water or other liquid carriers as described above.

Granular formulations include both extrudates and relatively coarse particles. Granular formulations are generally applied without dilution to a plant or growing site of a plant.

Typical carriers for granular formulations include, but are not limited to, fertilizer, sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or can be coated with the active compound.

Granular formulations normally contain one or more surface-active agents such as heavy aromatic naphthas, kerosene and other petroleum fractions, or vegetable oils; and/or stickers such as dextrins, glue, or synthetic resins. The granular substrate material can be a solid carriers described above and/or a fertilizer, such as urea/formaldehyde fertilisers, ammonium, liquid nitrogen, urea, potassium chloride, ammonium compounds, phosphorus compounds, sulphur, similar plant nutrients and micro nutrients and mixtures or combinations thereof.

The compounds may be homogeneously distributed throughout the granule or may be spray impregnated or absorbed onto the granule substrate after the granules are formed.

Encapsulated granules are generally porous granules with porous membranes sealing the granule pore openings, retaining the compounds in liquid form inside the granule pores.

Granules typically have a diameter ranging from about 1 mm to about 1 cm, such as from about 1 mm to about 50 mm, from about 1 mm to about 20 mm, from about 1 mm to about 10 mm, from about 1 mm to about 2 mm Granules are formed by extrusion, agglomeration or prilling, or are naturally occurring. Examples of naturally occurring granule materials include, but are not limited to, vermiculite, sintered clay, kaolin, attapulgite clay, sawdust, and granular carbon. Exemplary materials for porous membranes include, but are not limited to, natural and synthetic rubbers, cellulosic materials, styrene-butadiene copolymers, polyacrylonitriles, polyacrylates, polyesters, polyamides, polyureas, polyurethanes, and starch xanthates.

Dusts are free-flowing admixtures of the compounds with finely divided solids, such as talc, clays, flours and other organic and inorganic solids. The finely divided solids act as dispersants and carriers.

Microcapsules are typically droplets or granules where active compounds enclosed in an inert porous shell, which allows escape of the enclosed compounds to the surroundings at controlled rates.

Encapsulated droplets are typically about 1 to 50 microns in diameter. The enclosed liquid may include a liquid carrier as described above in addition to the compounds.

Other useful formulations include simple solutions of the compounds in a solvent in which it is completely soluble at the desired concentration, such as acetone, cyclohexanone, alkylated naphthalenes, xylene, and other organic solvents.

Pressurised sprayers, wherein the compounds are dispersed in finely-divided form as a result of vaporisation of a low boiling dispersant solvent carrier, may also be used.

II. Methods of Making and Using the Compositions

The synthetic path of the disclosed compounds is simple (only three steps), which significantly lower the cost and chemical waste, and can be used for large-scale preparation of SL analogs. The syntheic method for the compounds is significantly more effective than the synthesis of GR24, the widely applied SL analog, which typically takes 4-5 steps (Johnson et al., 1981; Mangnus et al., 1992a).

An exemplary method for making the compounds of Formulas I-VIII is described in Example 1.

Methods of using the compounds, or salts thereof, and formulations of the compounds or salts thereof are disclosed.

The disclosed compounds or salts thereof may be directly applied to a plant, a plant part, or a growing site of plant in an unmodified form. Alternatively, a formulation of the compounds or salts thereof is applied to the plant, the plant part, or the growing site of plant. Any formulations described above may be employed.

The disclosed compounds or salts thereof are highly effective in regulating plant growth (e.g., reducing number of tillering and dry biomasses, triggering dark-induced leaf senescence), and/or combating root parasitic plants. In some embodiments, the disclosed compounds can have higher efficiency in regulating plant architecture, (e.g., reducing number of tillering and dry biomasses and/or triggering dark-induced leaf senescence) and/or triggering parasitic seed germination (e.g., *Striga, P. aegptiaca*), compared to that of widely applied SL analog GR24.

Tillering, or branching from the nodes of shoots in plants such as monocots, is closely associated with crop yield because of its involvement in determining the final number of productive (grain bearing) and unproductive shoots. Excessive levels of tillering in the major cereal crops can lead to yield reductions because most of the tillers compete for resources with the main shoot during vegetative growth, but senesce before reaching maturity and so may not contribute to yield.

In some embodiments, the disclosed compounds can cause stunted growth and/or trigger senescence in the plant or plant part (e.g. seedlings or seeds), leading to reduced biomass and/or plant height.

A. Methods for Regulating Plant Growth

Generally, a method for regulating plant growth includes (i) applying one or more formulations described above to a plant, plant part, or growing site of plant.

Step (i) may be repeated, (e.g., more than once). Optionally, step (i) may be repeated twice, three times, four times, five times, six times, seven times, eight times, nine times, ten times, etc.

Generally, the plant, plant part, or growing site of plant can be treated with the one or more formulations for a period of time between one day and one month. In some embodiments, step (i) may be repeated during the entire treatment period. For example, the plant, plant part, or growing site of plant is treated with the one or more formulations for a total of three weeks, and step (i) is repeated twice per week. Alternatively, step (i) can be performed once during the entire treatment period. For example, the plant, plant part, or growing site of plant is treated with the one or more formulations for a total period of one day (i.e., 24 hours) or one week (i.e. 7 days), and step (i) is performed once at the beginning of the treatment.

Generally, the treatment can be performed at a temperature between about 20° C. and about 35° C., such as about 25 C or about 30° C. The specific temperature depends on the formulation form, application, and nature of the plants to be treated, which are known in the art.

Optionally, step (i) may be repeatedly applied to different parts of a plant and/or growing site of the plant at each time. For example, the one or more formulations may be applied to a seedling, seed of a plant, leaf of the plant, root of the plant, the growth medium before, during, and/or after incubating the plant, and/or the soil before, during, and/or after planting of the plant.

In some embodiments, the plant to be treated can be a cereal, grain, or vegetable plant. Exemplary plants include, but are not limited to, rice, corn, maize, wheat, barley, rye, oat, sorghum, pearl millet, millet, cotton, bean, soybean, pea, peanut, buckwheat, beet, rapeseed, sunflower, sugarcane, tobacco, solanaceous vegetables (eggplant, tomato, pimento, pepper, potato, etc.), hemp, clover, melon, legume, cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, dioscorea japonica, colocasia, etc.

In some preferred embodiments, the plant is a rice plant.

The plant may be wild-type or mutant. In some embodiments, the plant is a wild-type plant, preferably a wild-type rice plant.

In some embodiments, the plant is a SL deficient plant, such as a SL deficient rice plant, for example, d10/CCD8 and d3 rice mutants. In some embodiments, the one or more formulations, which are applied to the plant, plant part, or growing site of plant, contain an effective amount of the compounds or salts thereof to rescue a SL deficient plant, for example, by inhibiting tillering of the SL deficient plant.

The plant may be a mature plant or seedling. The formulations can be applied to seedlings, mature plants, or plant parts. Exemplary plant parts that can be treated include foliages, seeds, leaves, roots, and bulbs. Bulb generally refers to a bulb, corm, rhizoma, stem tuber, root tuber, and rhizophore.

In some embodiments, the formulations are applied to seedling, seed, or leaf of the plant.

The growing site of plant can be soil or a growing medium.

In some embodiments, the growing site of plant is soil. The soil may be soil before, during, or after planting the plant.

In some embodiments, the growing site of plant is a growing medium. Exemplary growing medium include, but are not limited to, water, buffer, culture solution, urethane, and rock wool. Culture solution generally refers to a water solution containing nutrient components required for plant growth.

The nutrient components and their relative concentrations can be easily adjusted to a proper concentration for different plants and application, which are known in the art.

The one or more formulations may be applied to a plant, plant part, or growing site of plant by any method known in the art, including both foliar and non-foliar application.

The one or more formulations may be applied before seeding, at the time of seeding, immediately after seeding, raising period, before settled planting, at the time of settled planting, and growing period after settled planting.

Exemplary application method to a plant or plant part include, but are not limited to, spraying, drenching, dripping on, or dusting the plant or plant part, coating a seed, and/or applying as a cream or paste or as a vapor.

For example, application methods for a foliage of plants may be applying to surfaces of plants, such as foliage spraying and trunk spraying. In some embodiments, the method of application can be absorbing to plants transplantation such as soaking entire plant, seedling, or plant part, such as seeds, leaves, or roots. In some embodiments, a formulation formulated with a solid carrier may be adhered to the roots.

Methods for coating a seed is known in the art, for example, US 2007/0105721 by Flematti, et al.

Exemplary application method to soil include, but are not limited to, spraying onto the soil, drenching the soil, dripping onto the soil, dusting the soil, and/or soil incorporation.

Examples of places where the one or more formulation can be applied include, but are not limited to, planting hole, furrow, around a planting hole, around a furrow, entire surface of cultivation lands, the parts between the soil and the plant, area between roots, area beneath the trunk, main furrow, growing soil, seedling raising box, seedling raising tray and seedbed.

Exemplary application method to a growing medium, such as a culture solution, include, but are not limited to, mixing the compounds or formulations into the growing medium.

The growing medium may be applied, for example, to soak a plant or plant part, such as seedlings or seeds for their rooting or germination, to soak leaves of plants or spray it to leaves to trigger senescence, or to soak roots of plants or spray it to roots to culture the plants.

Generally, the one or more formulations contain an effective amount of one or more the disclosed compounds or salts thereof to regulate plant growth. The term "effective amount" generally refers to the amount, concentration, or dosage of the one or more compounds or salts thereof sufficient to cause the desired results. For example, the one or more compounds or salts thereof in the one or more formulations are in an effective amount to inhibit tillering of the plant and/or trigger dark-induced leaf senescence. In some embodiments, the one or more compounds or salts thereof in the one or more formulations are in an effective amount to cause stunted growth and/or trigger senescence in the plant or plant part (e.g. seedlings or seeds), leading to reduced biomass and/or plant height. In some embodiments, the disclosed compounds are more effective than that of GR24 in regulating plant growth, such as inhibiting tillering of plant, triggering senescence, and/or causing stunted growth in plant at a similar dosage.

Generally, the one or more formulations can contain an effective amount of one or more the disclosed compounds or salts thereof from 0.1% to about 95% of the compounds or salts thereof by weight, such as between about 5% and about 95%, between about 0.1% and about 90% by weight, between about 1% and about 80% by weight, between about 1% and about 60% by weight, between about 1% and about 50% by weight, between about 1% and about 40% by weight, between about 1% and about 30% by weight, between about 1% and about 20% by weight, or between about 1% and about 10% by weight.

Alternatively, the one or more formulations can contain a concentration of compounds or salts thereof between about 0.1 μM and about 10 M, between about 1 μM and about 1 M, between about 1 μM and about 100 mM, or between about 1 μM and about 10 mM, such as up to about 1 M, up to about 500 mM, up to about 100 mM, at least 1 mM, at least 10 mM, or at least 50 mM. In some preferred embodiments, the one or more compounds or salts thereof in the formulation have a concentration between about 0.1 μM and about 100 μM, between about 0.1 μM and about 10 μM, between about 1 μM and about 10 μM, or between about 1 μM and about 5 μM, such as about 2.5 μM or about 3 μM.

In some embodiments, the one or more formulations are diluted before applying to a plant, plant part, or growing site of plant. In such cases, the concentration of the one or more compounds or salts thereof in the diluted formulation is between about 0.1 μM and about 1 mM, between about 0.1 μM and about 10 μM, or between about 1 μM and about 10 μM, such as about 2.5 μM or about 3 μM.

B. Methods for Combating Root Parasitic Plants

Generally, a method for combating root parasitic plants includes (i) applying one or more formulations described above to the root parasitic plant, a part of the root parasitic plant, or a growing site of root parasitic plant. Typically, the one or more compounds disclosed herein or salts thereof in the one or more formulation are in an effective amount to induce parasitic seed germination.

Step (i) may be repeated, (e.g., more than once). Optionally, step (i) may be repeated twice, three times, four times, five times, six times, seven times, eight times, nine times, ten times, etc.

Generally, the root parasitic plant, a part of the root parasitic plant, or a growing site of root parasitic plant can be treated with the one or more formulations for a period of time between one day and one month. In some embodiments, step (i) may be repeated during the entire treatment period. For example, the plant, plant part, or growing site of plant is treated with the one or more formulations for a total of three weeks, and step (i) is repeated twice per week. Alternatively, step (i) is performed once during the entire treatment period. For example, the plant, plant part, or growing site of plant is treated with the one or more formulations for a total period of one day (i.e., 24 hours) or one week (i.e. 7 days), and step (i) is performed once at the beginning of the treatment.

Generally, the treatment can be performed at a temperature between about 20° C. and about 35° C., such as about 25° C. or about 30° C.

The specific treatment period and temperature depends on the formulation form, application, and nature of the plants to be treated, which are known in the art. For example, seeds of *S. hermonthica* can be treated for about one day at about 30 C and seeds of *P. aegyptiaca* can be treated for about one week at about 25 C, to induce seed germination of the root parasitic plants.

Optionally, step (i) may be repeatedly applied to different parts of a root parasitic plant and/or growing site of root parasitic plant at each time. For example, the one or more formulations may be applied to a seed of a root parasitic plant, seedling of the root parasitic plant, the growth medium before, during, and/or after incubating the root parasitic plant, and/or the soil before, during, and/or after planting of the root parasitic plant.

1. Root Parasitic Plants

Root parasitic plants are known in the art.

In some embodiments, the root parasitic plant is a *Striga* species or a *Phelipanche* or *Orobanche* species of the Zygophyllaceae family. In some embodiments, the root parasitic plant is a *Striga* species, such as *S. hermonthica*. In some embodiments, the root parasitic plant is an *O. aegyptiaca* species, such as *P. ramosa.*

A root parasitic plant may be a seedling or a mature plant. A part of the root parasitic plant may be foliages, seeds, bulbs, and roots of the root parasitic plant. Preferably, the plant part of the root parasitic plant is seeds.

A growing site of root parasitic plant may be soil or a growing medium. In some embodiments, the growing site of root parasitic plant is soil before, during, or after planting a host plant. A host plant is generally the plant on which the root parasitic plant relies for its germination, nutrition, and/or water. In some embodiments, the growing site of the parasitic weed is soil before planting a host plant.

2. Applying the Formulations

The one or more formulations may be applied directly to a root parasitic plant, a part of root parasitic plant, or a growing site of root parasitic plant using any application methods described above.

Preferably, the method of application can be absorbing to plants transplantation such as soaking entire plant or plant part, such as seeds. For example, the method of application can be soaking seeds of parasitic weed plants in the one or more formulations formulated with liquid carriers, such as water or buffer. Alternatively, the method of application can be soaking seeds of parasitic weed plants in a growing medium in which the one or more formulations are applied, such as a culture solution, for their germination.

3. Optional Steps a. Applying Herbicides

The method may include a step of applying one or more herbicides before, during, or after step (i).

In some embodiments, one or more herbicides are applied prior to applying the one or more formulations of the compounds or salts thereof.

In some embodiments, the one or more herbicides are applied during (e.g., simultaneous or substantially simultaneous with) applying the one or more formulations of the compounds or salts thereof.

In some embodiments, the one or more herbicides are applied after applying the one or more formulations of the compounds or salts thereof.

Optionally, the herbicides may be part of a formulation described above, or independent from the one or more formulations.

4. Effective Amount

Generally, the one or more formulations contain an effective amount of one or more the disclosed compounds or salts thereof to combat root parasitic plants. Typically, the one or more disclosed compounds or salts thereof are in an effective amount to induce parasitic seed germination.

Generally, for inducing seed germination of the root parasitic plants, the one or more formulations can contain an effective amount of compounds or salts thereof from 0.1% to about 95% of the compounds or salts thereof by weight, such as between about 5% and about 95%, between about 0.1% and about 90% by weight, between about 1% and about 80% by weight, between about 1% and about 60% by weight, between about 1% and about 50% by weight, between about 1% and about 40% by weight, between about 1% and about 30% by weight, between about 1% and about 20% by weight, or between about 1% and about 10% by weight.

Alternatively, the one or more formulations can contain a concentration of compounds or salts thereof between about 0.1 μM and about 10 M, between about 1 μM and about 1 M, between about 1 μM and about 100 mM, or between about 1 μM and about 10 mM, such as up to about 1 M, up to about 500 mM, up to about 100 mM, at least 1 mM, at least 10 mM, or at least 50 mM. In some preferred embodiments, the one or more compounds or salts thereof in the formulation have a concentration between about 0.1 μM and about 100 μM, between about 0.1 μM and about 10 μM, between about 1 μM and about 10 μM, or between about 1 μM and about 5 μM, such as about 2.5 μM or about 3 μM.

In some embodiments, the one or more formulations are diluted before applying to a parasitic weed, part of parasitic weed, or growing site of parasitic weed. In such cases, the concentration of the one or more compounds or salts thereof in the diluted formulation is between about 0.1 μM and about 1 mM, between about 0.1 μM and about 10 μM, or between about 1 μM and about 10 μM, such as about 3 μM.

The disclosed compounds and methods can be further understood through the following numbered paragraphs.

1. A compound having the structure of Formula I:

Formula I

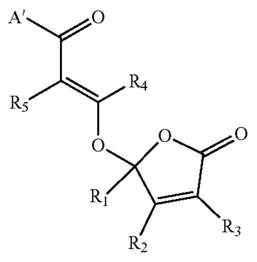

(a) wherein A' is an alkoxy group containing one substituent, an amino group optionally containing one or two substituents at the amino nitrogen, or a thiol group optionally containing one substituent at the thiol sulfur;

(b) wherein $R_1$-$R_4$ are independently a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group; and (c) wherein $R_5$ is an unsubstituted alkyl group, a substituted alkyl group, an unsubstituted cycloalkyl group, a substituted cycloalkyl group, an unsubstituted heteroalkyl group, a substituted heteroalkyl group, an unsubstituted cycloheteroalkyl group, a substituted cycloheteroalkyl group, an unsubstituted alkenyl group, a substituted alkenyl group, an unsubstituted heteroalkenyl group, a substituted heteroalkenyl group, a substituted alkynyl group, a substituted heteroalkynyl group, an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, or a substituted polyheteroaryl group, an unsubstituted alkylaryl group, or a substituted alkylaryl group. 2. The compound of paragraph 1 having the structure of Formula II:

Formula II

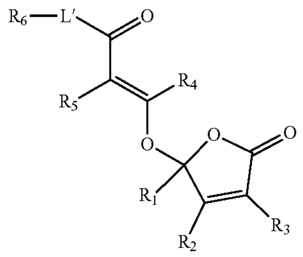

(a) wherein $R_1$-$R_4$ are as defined in paragraph 1;

(b) wherein L' is an oxygen atom or a sulfur atom; and (c) wherein $R_5$ and $R_6$ are independently an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group, wherein the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

3. The compound of paragraph 1 or paragraph 2 having the structure of Formula III:

Formula III

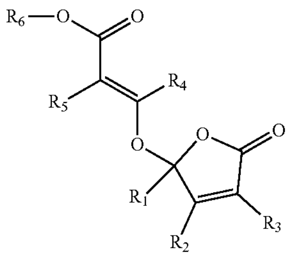

(a) wherein $R_1$-$R_4$ are independently a hydrogen atom, a halogen atom, an alkyl group, a hydroxyl group, or an amino group;

(b) wherein $R_5$ and $R_6$ are independently an unsubstituted aryl group, a substituted aryl group, an unsubstituted polyaryl group, a substituted polyaryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

4. The compound of any one of paragraphs 1-3 having the structure of Formula IV:

Formula IV

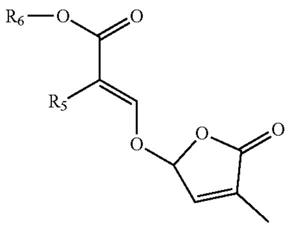

(a) wherein $R_5$ is an unsubstituted aryl group or a substituted aryl group; and (b) wherein $R_6$ is an unsubstituted aryl group, a substituted aryl group, an unsubstituted polyaryl group, a substituted polyaryl group, an unsubstituted alkylaryl group, or a substituted alkylaryl group, wherein the substituents are independently a halogen atom or an alkyl group.

5. The compound of any one of paragraphs 1-4 having the structure of Formula V:

Formula V

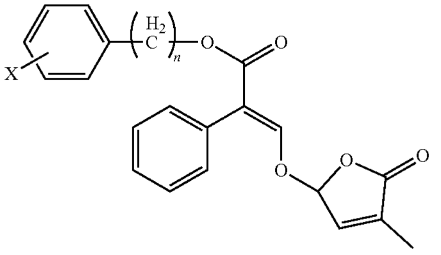

(a) wherein n is 0 or a positive integer between 1 and 5; and
(b) wherein X is a hydrogen atom, a halogen atom, or an alkyl group.

6. The compound of any one of paragraphs 1-4, wherein $R_5$ is an unsubstituted aryl group, and $R_6$ is an unsubstituted polyaryl group.

7. The compound of paragraph 1 having the structure of Formula VI:

Formula VI

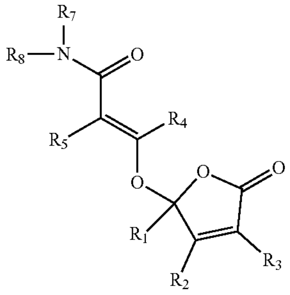

(a) wherein $R_1$-$R_4$ are as defined in paragraph 1;
(b) wherein $R_5$ is an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group; and
(c) wherein $R_7$ and $R_8$ are independently a hydrogen atom, an unsubstituted alkyl group, a substituted alkyl group, an unsubstituted heteroalkyl group, a substituted heteroalkyl group, an unsubstituted alkenyl group, a substituted alkenyl group, an unsubstituted heteroalkenyl group, a substituted heteroalkenyl group, an unsubstituted alkynyl group, a substituted alkynyl group, an unsubstituted heteroalkynyl group, a substituted heteroalkynyl group, an unsubstituted aryl group, a substituted aryl group, an unsubstituted an unsubstituted heteroaryl group, or a substituted heteroaryl group, wherein the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

8. The compound of paragraph 7, (a) wherein $R_1$-$R_4$ are independently a hydrogen atom, a halogen atom, an alkyl group, a hydroxyl group, or an amino group;
(b) wherein $R_5$ is an unsubstituted aryl group, a substituted aryl group, an unsubstituted polyaryl group, a substituted polyaryl group, an unsubstituted alkylaryl group, or a substituted alkylaryl group; and
(c) wherein $R_7$ and $R_8$ are independently a hydrogen atom, an unsubstituted alkyl group, a substituted alkyl group, an unsubstituted heteroalkyl group, a substituted heteroalkyl group, an unsubstituted aryl group, a substituted aryl group, an unsubstituted heteroaryl group, a substituted heteroaryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

9. The compound of paragraph 7 or paragraph 8 having the structure of Formula VII:

Formula VII

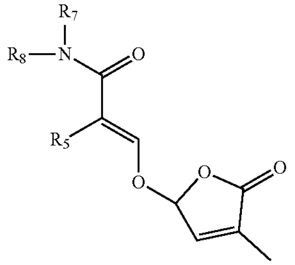

(a) wherein $R_5$ is an unsubstituted aryl group or a substituted aryl group; and
(b) wherein $R_7$ and $R_8$ are independently a hydrogen atom, an unsubstituted alkyl group, a substituted alkyl group, an unsubstituted aryl group, a substituted aryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

10. The compound of any one of paragraphs 7-9 having the structure of Formula VIII:

Formula VIII

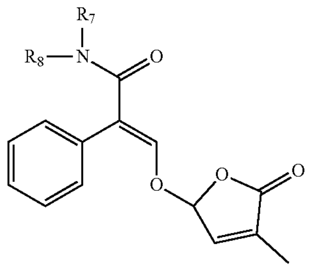

wherein $R_7$ and $R_8$ are independently a hydrogen atom, an unsubstituted alkyl group, or a substituted alkyl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

11. A compound having a structure of:

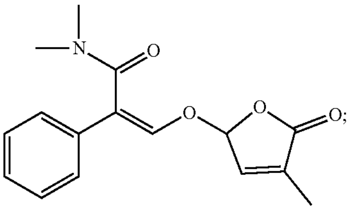

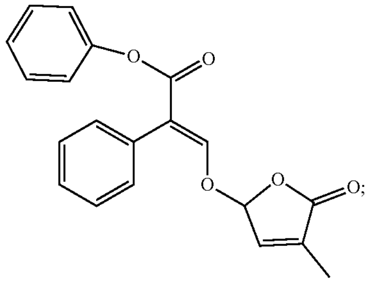

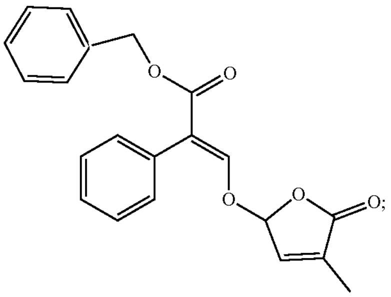

-continued

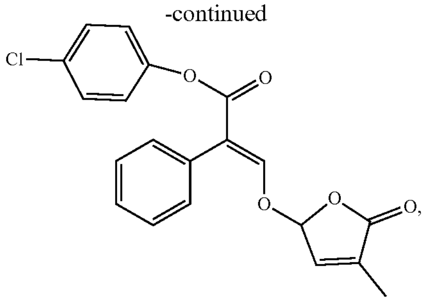

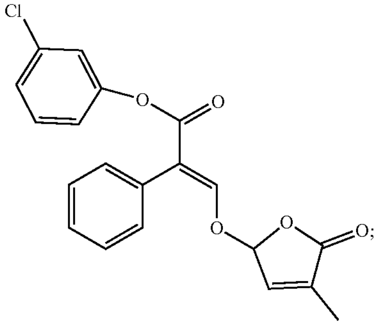

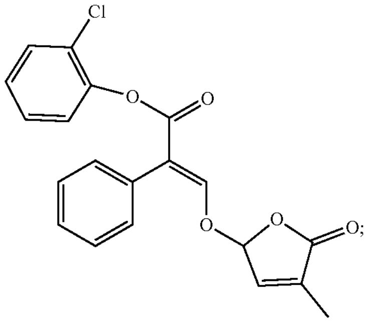

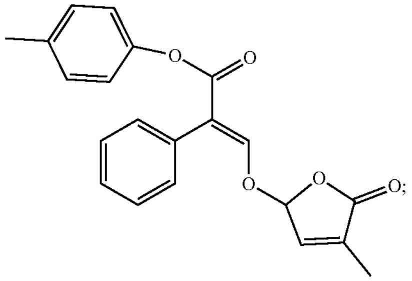

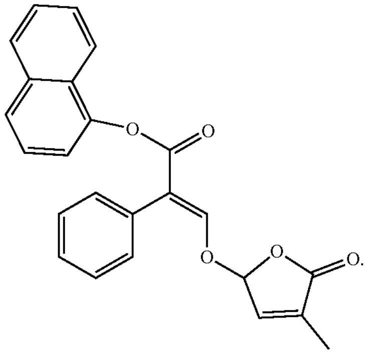

12. A method of regulating plant growth comprising applying one or more formulations to a plant, a plant part, or a growing site of plant, wherein the one or more formulations comprise:

(a) one or more compounds of any one of paragraphs 1-11, or salts thereof, and (b) one or more formulation excipients, wherein the one or more compounds or salts thereof are in an effective amount to regulate plant growth.

13. The method of paragraph 12, wherein the one or more compounds or salts thereof are in an effective amount to inhibit tillering of the plant.

14. The method of paragraph 12 or paragraph 13, wherein the one or more compounds or salts thereof are in an effective amount to trigger dark-induced leaf senescence.

15. A method of combating root parasitic plants comprising applying one or more formulations to a root parasitic plant, a plant part of root parasitic plant, or a growing site of root parasitic plant, wherein the one or more formulations comprise:

(a) one or more compounds of any one of paragraphs 1-11, or salts thereof, and (b) one or more formulation excipients, wherein the one or more compounds or salts thereof are in an effective amount to induce seed germination of the root parasitic plant.

The present invention will be further understood by reference to the following non-limiting examples.

EXAMPLES

The Examples below demonstrated highly effective Strigolactone (SL) analogs that regulate plant growth and/or combat root parasitic plants. These exemplary compounds can be prepared by simple synthesis, and show high efficiency in regulating plant growth and architecture (e.g., shoot branching/tillering, triggering dark-induced leaf senescence), and combating root parasitic plants (e.g., *Striga* and *Phelipanche aegyptiaca*). The synthesis of these SL analogs is simple compared to the widely used SL analog GR24 (Johnson et al., 1981; Mangnus and Zwanenburg, 1992; Mangnus et al., 1992a; Rasmussen et al., 2013)). The exemplary compounds can have higher efficiency in regulating plant architecture, such as reducing number of tillering and dry biomasses, as well as inducing parasitic seed germination, such as *P. aegptiaca*, compared to that of GR24.

Example 1. Synthesis of SL Analogs

Materials and Methods

Preparation of Esters and Amide

Phenylacetyl chloride (3 mmol) was added dropwise to the solution of pyridine (10 ml) and alcohol or phenol (10 mmol) with stirring in a 50 ml of round-bottom flask in an ice bath (Scheme 1). The mixture was stirred at room temperature overnight then poured into ice-cold water (10 ml). The organic layer was extracted with ethyl acetate (5 ml×3), washed with saturated brine (20 ml), dried over anhydrous sodium sulfate, and filtered. The organic solvent was evaporated under reduced pressure and the residue was then purified on a silica gel (Wakosil®C-300HG) column eluted with ethyl acetate/n-hexane to give an ester (53-95% yield). The preparation of amide compound followed the same step as described above, except dimethyl amine was used as the starting material instead of alcohol (78% yield).

Preparation of SL Analogs

To an ice-cold solution of the ester (2.47 mmol) obtained above, methyl formate (7.91 mmol) and trimethylamine (5.93 mmol) in dichloromethane (15 ml), titanium(IV) chloride (4.94 mmol) were added slowly and stirred for 10 min (Scheme 2). The mixture was stirred further for 2 h at room temperature and then poured into ice-cold water (10 ml). The organic layer was extracted with ethyl acetate (5 ml×3), washed with saturated brine (20 ml), dried over anhydrous sodium sulfate, and filtered. The organic solvent was evaporated under reduced pressure and the residue was then purified on a silica gel (Wakosil®C-300HG) column eluted with ethyl acetate/n-hexane to give aldehyde. All of the compounds thus obtained were used in the next step without measuring weight. To an ice-cold solution of the aldehyde obtained above in dichloromethane (13 ml), 5-bromo-3-methyl-2(5H)-furanone (2.47 mmol) and trimethylamine (3.71 mmol) was added and stirred overnight at room temperature and then poured into ice-cold water (10 ml). The organic layer was extracted with ethyl acetate (5 ml×3), washed with saturated brine (20 ml), dried over anhydrous sodium sulfate, and filtered. The organic solvent was evaporated under reduced pressure and the residue was then purified on a silica gel (Wakosil®C-300HG) column eluted with ethyl acetate/n-hexane to give enolether. MP17, MP 18, and MP 21-25 (structures shown above) were prepared according to the method above (10-67% yield). The preparation of MP16 followed the same step as described above, except the amide compound was used as the starting material instead of ester (21% yield). $^{1}H$, $^{13}C$ NMR and HRMS spectra of all synthesized compounds were recorded on JEOL JNM-ECA500II 500 MHz spectrometer and ABSciex TripleTOF5600 Q-TOF LC/MSMS. Z/E stereochemistry was assigned based on NOE experiments. In case of the E-isomer (MP16) NOE between vinyl proton and aromatic proton was observed. In case of Z-isomer NOE between vinyl proton and aromatic proton was not observed and instead NOE between vinyl proton and methyl proton of carbomethoxy group was observed.

Results

Scheme 1. synthesis of esters and amide

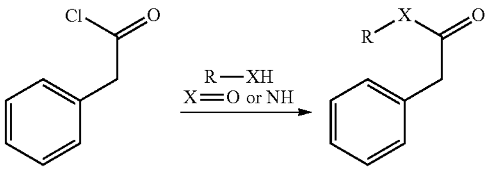

Phenylacetyl chloride

Scheme 2. synthesis of SL analogs

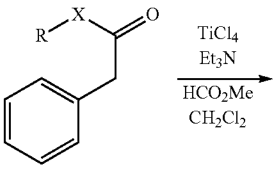

-continued

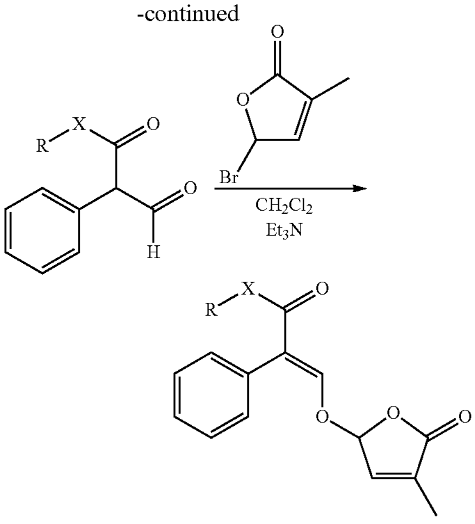

The physico-chemical properties of the SL analogs are as follows:

MP16 ((Z)—N,N-Dimethyl-3-((4-methyl-5-oxo-2,5-dihydrofuran-2-yl)oxy)-2-phenylacrylamide)

$^1$H NMR (500 MHz, $CDCl_3$): δ 7.27 (5H, m), 6.93 (1H, s), 6.77 (1H, s), 6.09 (1H, s), 3.03 (3H, s), 2.91 (3H, s), 1.97 (3H, s). HRMS (m/z): [1\4+H]$^+$ calcd. for $C_{16}H_{18}NO_4$, 288.1230; found, 288.1231. 21% Yield.

MP17 ((E)-Phenyl 3-((4-methyl-5-oxo-2,5-dihydro-furan-2-yl)oxy)-2-phenylacrylate)

$^1$H NMR (500 MHz, $CDCl_3$): δ 7.98 (1H, s), 7.40 (5H, m), 7.32 (1H, m), 7.24 (1H, t, J=7.5 Hz), 7.38 (2H, d, J=5.5 Hz), 6.90 (1H, s), 6.20 (1H, s), 2.00 (3H, s). HRMS (m/z): [M+H]$^+$ calcd. for $C_{20}H_{17}O_5$, 337.1071; found, 337.1069. 38% Yield.

MP18 ((E)-Benzyl 3-((4-methyl-5-oxo-2,5-dihydro-furan-2-yl)oxy)-2-phenylacrylate)

$^1$H NMR (500 MHz, $CDCl_3$): δ 7.76 (1H, s), 7.33 (10H, m), 6.84 (1H, s), 6.12 (1H, s), 5.22 (2H, s), 1.96 (3H, s). HRMS (m/z): [M+Na]$^+$ calcd. for $C_{21}H_{18}NaO_5$, 373.1046; found, 373.1051. 67% Yield.

MP21 ((E)-Benzyl 3-((4-methyl-5-oxo-2,5-dihydro-furan-2-yl)oxy)-2-phenylacrylate)

$^1$H NMR (500 MHz, $CDCl_3$): δ 7.96 (1H, s), 7.30-7.40 (7H), 7.07 (2H, d, J=8.5 Hz), 6.90 (1H, s), 6.20 (1H, s), 1.99 (3H, s). HRMS (m/z): [M+H]$^+$ calcd. for $C_{20}H_{16}ClO_5$, 371.0681; found, 371.0675. 11% Yield.

MP22 ((E)-3-Chlorophenyl 3-((4-methyl-5-oxo-2,5-dihydrofuran-2-yl)oxy)-2-phenylacrylate)

$^1$H NMR (500 MHz, $CDCl_3$): δ 7.96 (1H, s), 7.39 (4H, d, J=4.5 Hz). 7.33 (2H, m), 7.22 (1H, d, J=8.0 Hz), 7.18 (1H, t, J=2.5 Hz), 7.05 (1H, d, J=8.0 Hz), 6.90 (1H, s), 6.21 (1H, s), 2.00 (1H, s). HRMS (m/z): [M±Na]$^+$ calcd, for $C_{20}H_{15}ClNaO_5$, 393.0500; found, 393.0498. 10% Yield.

MP23 ((E)-2-Chlorophenyl 3-((4-methyl-5-oxo-2,5-dihydrofuran-2-yl)oxy)-2-phenylacrylate)

$^1$H NMR (500 MHz, $CDCl_3$): δ 8.03 (1H, s), 7.45 (3H, d, T=8.5 Hz), 7.38 (2H, t, T=7.0 Hz), 7.25-7.34 (2H), 7.19 (2H, m), 6.90 (1H, s), 6.21 (1H, s), 2.00 (3H, s). HRMS (m/z): [M+Na]$^+$ calcd. for $C_{20}H_{15}ClNaO_5$, 393.0500; found, 393.0501. 32% Yield.

MP24 ((E)-p-Tolyl 3-((4-methyl-5-oxo-2,5-dihydro-furan-2-yl)oxy)-2-phenylacrylate)

$^1$H NMR (500 MHz, $CDCl_3$): δ 7.95 (1H, s), 7.36 (5H, m), 7.17 (2H, d, J=8.0 Hz), 6.89 (1H, s), 6.20 (1H, s), 2.34 (3H, s), 1.99 (3H, s). HRMS (m/z): [M+H]$^+$ calcd. for $C_{21}H_{19}O_5$, 351.1227; found, 351.1223. 10% Yield.

MP25 ((E)-naphthalen-1-yl 3-((4-methyl-5-oxo-2,5-dihydrofuran-2-yl)oxy)-2-phenylacrylate)

$^1$H NMR (500 MHz, $CDCl_3$): δ 8.11 (1H, s), 7.84 (2H, m), 7.74 (1H, d, J=8.0 Hz), 7.28-7.54 (9H), 6.92 (1H, s), 6.24 (1H, s), 2.00 (3H, s). HRMS (m/z): [1\4+H]$^+$ calcd. for $C_{24}H_{19}O_5$, 387.1227; found, 387.1209. 55% Yield.

Example 2. The SL Analogs are Stable

Materials and Methods

Three selected MPs (MP16, MP18, MP21) and rac-GR24 were tested for their chemical stability at 21±1° C. in aqueous solution with a pH of 5.5-6.0, as described previously (Jamil et al., 2018). Compound solution (1 mg ml$^{-1}$) was prepared with 175 μl ethanol and 750 μl Mili-Q water. Thereafter, 25 μl Indanol (1 mg ml$^{-1}$, internal standard) was spiked in 975 μl previous prepared solution. The time course of degradation was monitored in about 50 μl aliquots by UPLC analysis using an Agilent HPLC ZORBAX Eclipse XDB-C18 column (3.5 nm, 4.6×150 mm) eluted first by 5% acetonitrile in water for 0.5 min then by a gradient from 5% to 100% acetonitrile within 18 min in water, and finally by 100% acetonitrile for 5 min. The column was operated at 40° C. at 035 ml min$^{-1}$ flow rate. Compounds eluted from the column were detected with a photodiode array detector, and the relative quantity of non-degraded amount was calculated using Indanol as internal standard. Stability was monitored at 24 h intervals up to 3 weeks.

Results

Figure 7:
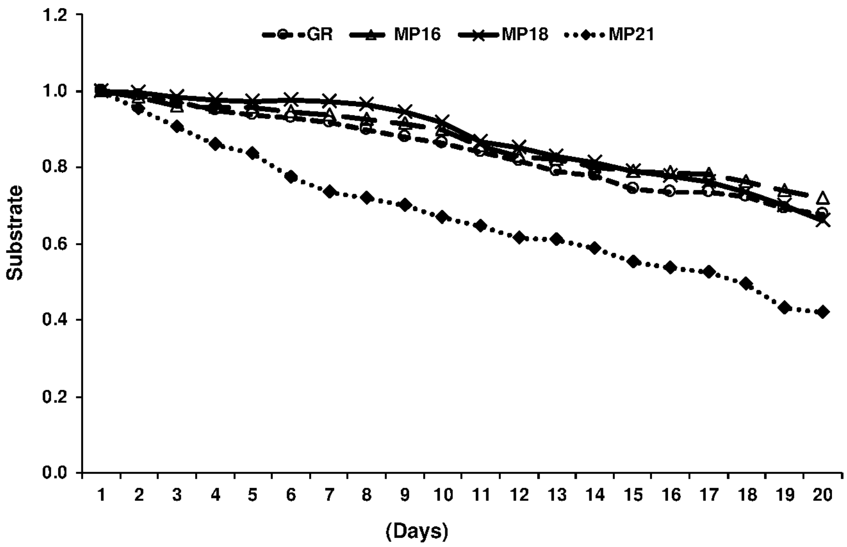
FIG. 7 is a graph showing stability of MP16, MP18, MP21, and GR24 (GR) measured by HPLC. The relative amount of non-degraded MP16, MP18, MP21, and GR24 was monitored in HPLC on daily basis upto 3 weeks and determined by comparison with internal standard. Data are means±SE (n=3). X-axis (time (days)); Y-axis (substrate).

Stability is an important feature that impacts biological activity of SL analogs. The stability of MP16, MP18, and MP21 was determined in aqueous solution (pH 5.5-6.0), in comparison with the standard SL analog GR24. The stability of MP16 and MP18 was in the range of that of GR24, while MP21 showed a higher degradation rate, compared to GR24 (FIG. 7), which might be a reason for its low performance.

Example 3. The SL Analogs Possess High Activity in Plant Growth Regulation

Materials and Methods

Plant Materials and Growth Conditions

*Striga hermonthica* seeds were provided by Prof. Abdel Gabar Babiker collected from Sorghum infested field near Wad Medani, Sudan. Seeds of *Phelipanche aegyptiaca* were provided by Prof. Mohamed Ewis Abdelaziz, Cairo University, Egypt. Seeds of the highly *Striga* susceptible rice cv IAC 165 are a gift from Dr. Jonne Rodenburg, Africa Rice, Tanzania. Dr. Junko Kyozuka, Tohoku University, Japan provided us with seeds of the rice d10 and d3 mutants. Rice seeds were germinated at 30° C. on moist filter paper, and seedlings were grown at 30° C. and 70% relative humidity with fluorescent white light (130-180 μM $m^{-2}$ $s^{-1}$) 12 h day/night period. *Striga* and *Phelipanche* seeds pre-conditioning was done under moist conditions in the dark at 30° C. and 22° C., respectively.

Rice Micro Tillering Bioassays

After sterilization with 50% sodium hypochlorite, rice seeds (d10/CCD8 and d3 mutants) were germinated on moist filter paper in the dark at 30° C. The germinated seeds were then transferred to light in a growth cabinet with fluorescent white light (130-180 μM $m^{-2}$ $s^{-1}$) at 30° C. for seven days. One-week old rice seedlings were shifted to 50 ml falcon tubes (one seedling per tube) filled with half-strength modified Hoagland nutrient solution. The tubes with rice seedlings were kept in green house to grow at 30° C. and 70% humidity. After one week, the rice seedlings were treated with 2.5 μM of each SL analog. Mock and GR24 (2.5 μM) were included as control treatments. Each of the SL analogs (MPs 16-18 and 21-25) was applied twice per week up to three weeks. Number of tillers per plant, plant height and dry biomass were measured after three weeks of SL analogs application at final harvest.

Statistical Analyses

Standard procedure was adopted to collect data for each trait, which were analyzed statistically using statistical software package R (version 3.2.2). One-way analysis of variance (ANOVA) and LSD (Least significant difference) multiple range test were applied to investigate the effect of various SL analogs (MPs 16-18 and 21-25) for various parameters. Half Maximum Effective Concentration ($EC_{50}$) was calculated using $IC_{50}$ toolkit (http://www.ic50.tk/index.html).

Results

Figure 1B:
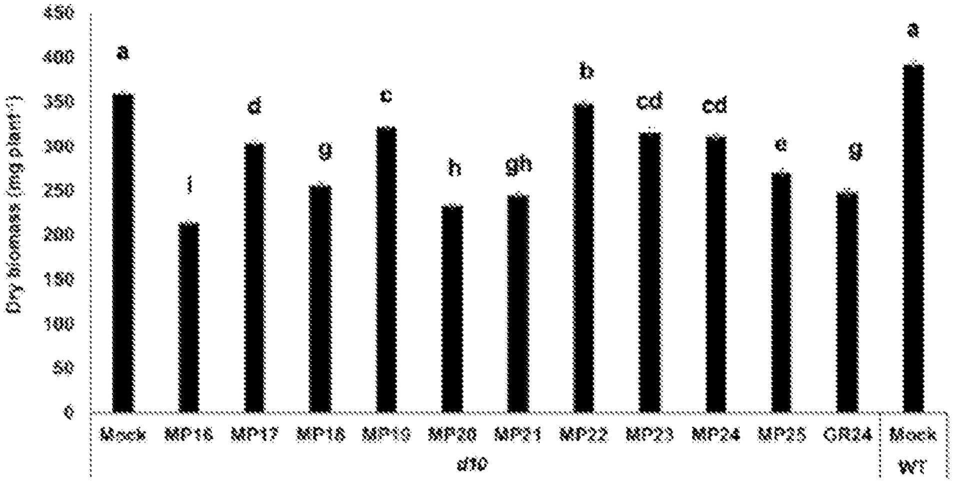
Figure 2A:
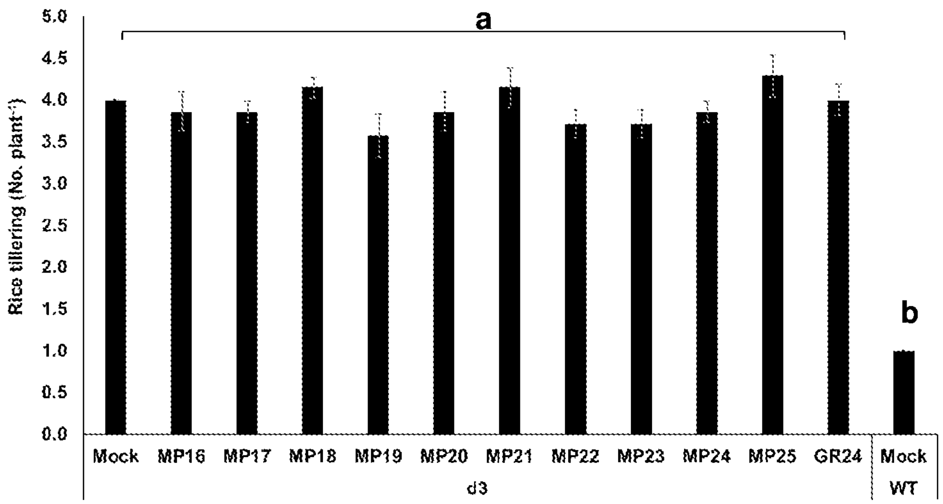
FIGS. 2A-2B are bar graphs showing tillering inhibition in SL insensitive d3 rice mutant by MP16-MP25.
Figure 2B:
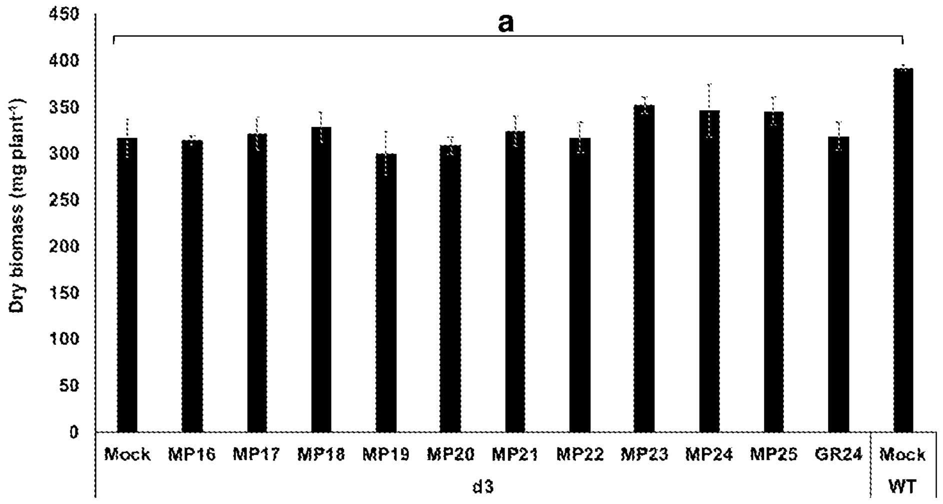

The activity of these SL analogs (MPs 16-18 and 21-25) in regulating the growth and architecture of rice was tested. MP19 and MP20 were tested under the same conditions for comparison (the structures of MP19 and MP20 are shown below). Since shoot branching/tillering inhibition is the best known hormonal function of SLs (Gomez-Roldan et al., 2008; Umehara et al., 2008), the SL analogs were applied at a 2.5 μM concentration to hydroponically grown seedlings of the high tillering SL deficient d10/CCD8 and SL insensitive d3 rice mutants. All MP compounds showed statistically significant effect in inhibiting tillering of the SL deficient d10 mutant, compared to mock treatment (FIGS. 1A-1B). The MP compounds also showed decrease in dry biomasses. MPs 16-18 restored wild-type tillering to the d10 mutant, decreasing the number of its tillers from 5 (untreated) to 1, with similar efficiency as GR24. MP16 is more effective compared with MPs 19 and 20. Neither MP compounds nor GR24 (a widely applied SL analog) showed an effect on the tillering of the SL insensitive d3 mutant that retained an average of 4 tillers per plant regardless treatment (FIGS. 2A-2B).

Figure 3:
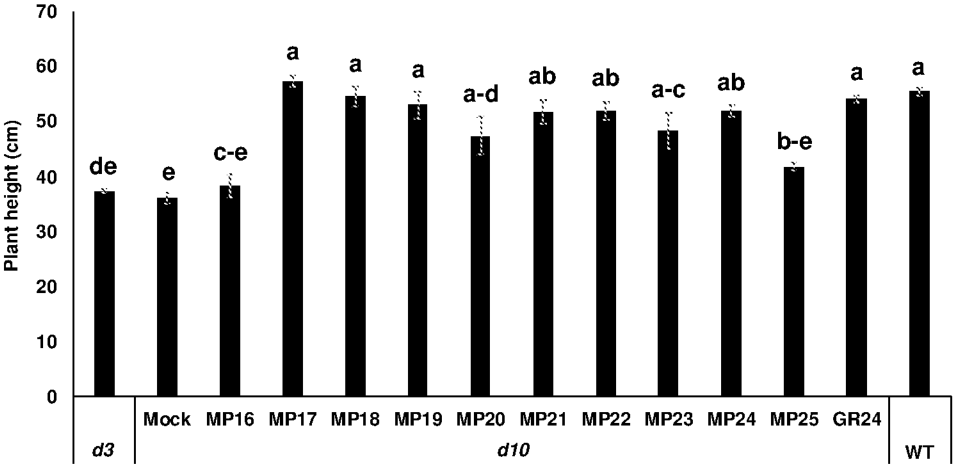
FIG. 3 is a bar graph showing effect of MP compounds on d10 rice plant height. All the MP compounds were applied (2.5 μM) to one-week old hydroponically grown rice seedlings (d10/CCD8 mutant) twice a week up to three weeks. Plant height per plant were measured (n=8) and compared by one-way ANOVA. Means not sharing a letter in common differ significantly at $P_{0.05}$.

Besides reducing the number of tillers, the effect of MP16 (applied at a 2.5 μM concentration) was even more drastic than that of GR24, causing stunted growth and triggered senescence in rice seedlings, leading to reduced biomass and plant height (FIG. 3). This result shows that MP16 possesses high activity in growth regulation and senescence. The high activity of MP16 makes it a very good candidate for application as structurally simple growth regulator.

MP19

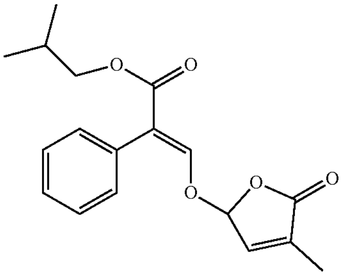

MP20

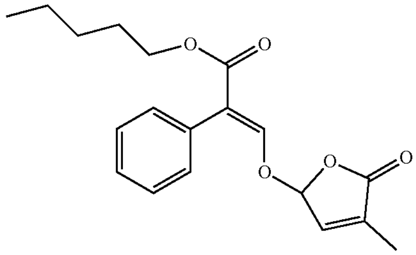

Example 4. The SL Analogs Show Activity in Triggering Dark-Induced Leaf Senescence Materials and Methods Rice seeds (cv IAC-165) were surface sterilized with 50% sodium hypochlorite solution and 0.05% Tween-20, and germinated on moist filter paper in the sealed petri plates. The petri plates with germinated seeds were transferred to white fluorescent light (130-180 μM $m^{-2}$ $s^{-1}$) with 16 h:8 h (L/D) at 28° C., to establish seedlings for one week. Seven days old uniform seedlings were selected and transferred to 50 ml tubes containing half strength modified Hoaglands nutrient solution. After one week, 2 cm leaf segments were cut from middle part of third leaves of rice plants. Each segment was put in a well (in 12-well plates) containing 4 ml of 3.0 mM MES buffer with 0.05% Tween-20. MP16 and GR24 were applied at 3.0 μM concentration. Plates were incubated at 30° C. in the dark for 7 days. After application of MP16 and GR24, plates were monitored on a daily basis and changes in leaf color, chlorophyll content and ion leakage were monitored.

Results

Figure 4A:
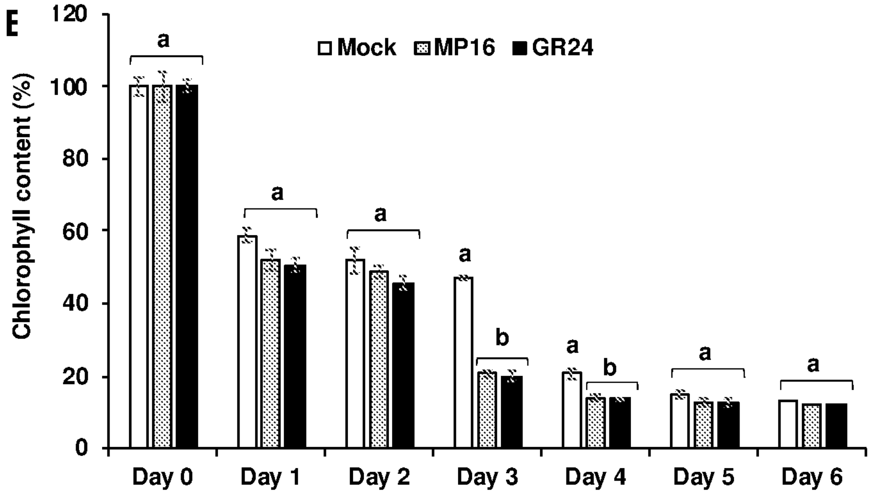
FIGS. 4A-4B are bar graphs showing dark-induced leaf senescence in response to MP16 and GR24.
Figure 4B:
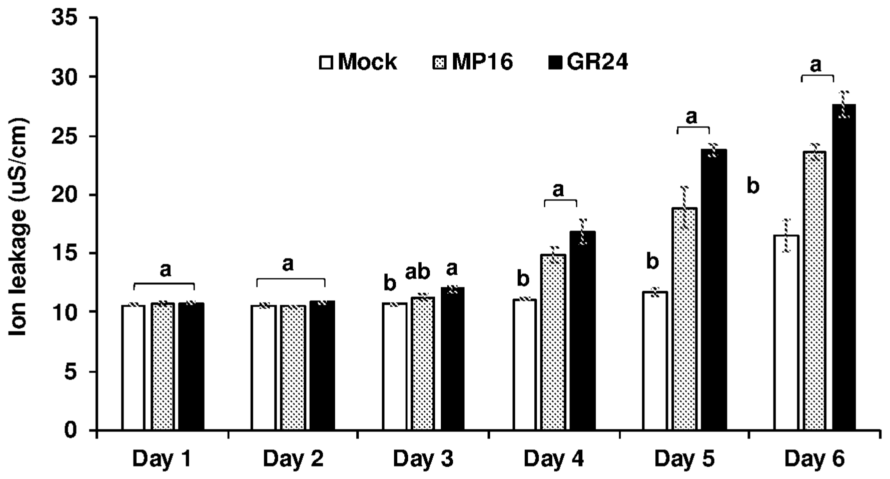

The activity of MP16 in triggering dark-induced leaf senescence was investigated in comparison to the standard SL analog GR24. MP16 and GR24 treated leaf segments showed a loss of the green color on the third day after application, which was one day earlier than mock control (Data not shown). Accordingly, measurement of the chlorophyll content showed a significant reduction in GR24 and MP16 treated segments on the third and fourth day of treatment (FIG. 4A). In both GR24 and MP16 treated leaf segments, the ion leakage, an indicator of the loss of membrane integrity, began to increase on the third day of treatment and continued to increase till day 6 (FIG. 4B).

MP16 shows an activity similar to that of GR24, i.e. the application of MP16 accelerated the leaf senescence process, leading to a color loss after two days. Other senescence parameters, such as chlorophyll content and electrolytes leakage, were changed to a similar extent upon MP16 and GR24 application (FIGS. 4A-4B).

Example 5. The SL Analogs Show High Activity in Inducing Seed Germination in Root Parasitic Plants Materials and Methods Parasitic Seed Germination Bioassays Seeds of the two root parasitic species *S. hermonthica* and *P. aegyptiaca* were tested for germination in response to MP compounds application. After pre-conditioning, as previously described (Jamil et al., 2012), *Striga* and *Phelipanche* seeds were first tested with each MP solutions at 2.5 μM concentration (55 μl per disc) and then at a concentration range from $10^{-5}$M to $10^{-12}$M, to calculate $EC_{50}$. Sterile MilliQ water and GR24 were applied as a negative and a positive control, respectively. Treated seeds were incubated in dark for 24 h at 30° C. (for *S. hermonthica*) and for one week at 25° C. (for *P. aegyptiaca*). Germination was recorded under a binocular microscope and used to determine the germination rate (%).

Results

Root parasitic plants, in particular *S. hermonthica*, are causing huge damage in African agriculture and are considered as a major threat to global food security. Infested fields have accumulated huge amounts of long-living and tiny seeds (Rubiales et al., 2009), which represent a major constraint in combating *Striga* and related species. Induction of suicidal germination of root parasitic seeds is a promising approach to combat these weeds in Africa and other parts of the world (Samejima et al., 2016; Zwanenburg et al., 2016a; Kountche et al., 2019). This approach requires efficient and easy-to-synthesize SL analogs and is a major potential application field for these chemistries.

Figure 5A:
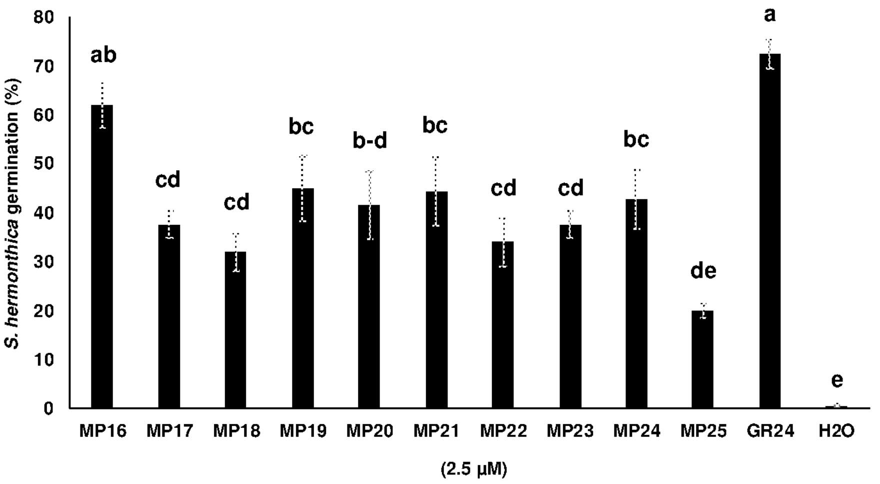
FIGS. 5A-5B are bar graphs showing *S. hermonthica* (FIG. 5A) and *P. aegyptiaca* (FIG. 5B) seed germination in response to MP compounds application. Each MP compound (2.5 μM) was applied in 55 μl volume on a disc containing 50-100 preconditioned *S. hermonthica/P. aegyptiaca* seeds. GR24 and $H_2O$ are included as positive and negative control, respectively. Bars represent means±SE (n=6). Means not sharing a letter in common differ significantly at $P_{0.05}$.
Figure 5B:
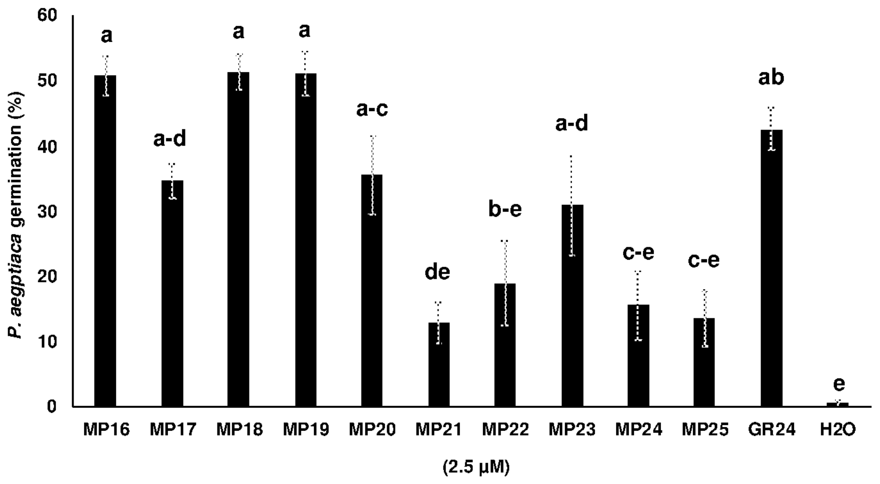

The activity of the SL analogs (MP16-18 and 21-25) in inducing seed germination in root parasitic plants was tested. MP19 and MP20 were tested under the same conditions for comparison. The MP compounds were applied to pre-conditioned *S. hermonthica* seeds and the rate of germination was determined (FIG. 5A). Application of MP16 at a 2.5 μM concentration resulted in a high *Striga* germination rate (62%), which was comparable to that of GR24 (72%). The germination rate of MP16 is higher than MPs 19 and 20. Application of other MP compounds (MP17, 18, and 21-25) led generally to lower germination rate. Germination inducing activity of MP16-18 and 21-25 on seeds of *Phelipanche aegyptiaca* was also tested. Application of MP16 and MP18 at 2.5 μM concentration caused very high germination rates (around 51%), which was statistically equal to that observed upon treatment with GR24 (43%) (FIG. 5B). MP19 applied at 2.5 μM shows comparable germination rate as MPs 16 and 18, and is much higher than MP20. MP21, MP22, MP24 and MP25, showed lower activity in inducing *Phelipanche* seed germination. These results show that the SL analogs described in the present study are effective in combating different root parasitic species.

Figure 6:
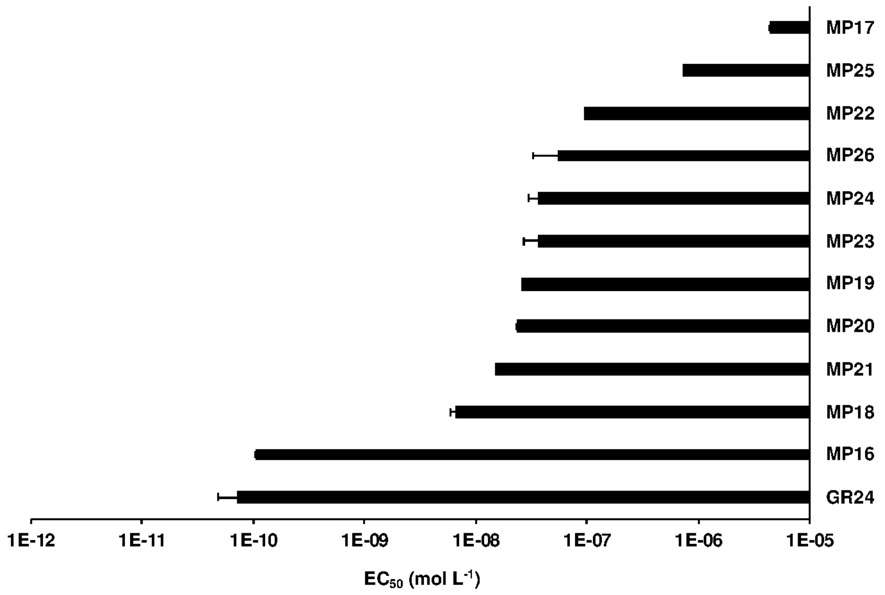
FIG. 6 is a bar graph showing Half Maximal Effective Concentration (EC50) of MP16-MP25 for *Striga* seed germination. Preconditioned *S. hermonthica* seeds were treated with 55 μl of aqueous solutions of each MP compound, with various concentrations ranging from $10^{-5}$M to $10^{-12}$M on a disc containing 50-100 pre-conditioned *Striga* seeds. GR24 is included as positive control.

For a better quantification of *Striga* seed germination inducing activity, the half maximal effective concentration ($EC_{50}$) of the different SL analogs (MP16-18 and 21-25) was determined (FIG. 6). MP19 and MP20 were tested under the same conditions for comparison. The standard analog GR24 showed the lowest $EC_{50}$ value of $7.23\times10^{-11}$ mol $L^{-1}$ for *Striga* germination. MP16 was the second-best analog in this assay, with an $EC_{50}$ value of $1.05\times10^{-10}$ mol $L^{-1}$, followed by MP18, ($EC_{50}$ value of $6.44\times10^{-9}$ mol $L^{-1}$). The $EC_{50}$ value of MP16 ($EC_{50}$=$1.05\times10^{-10}$ mol $L^{-1}$) is less than two times higher than that of GR24 ($EC_{50}$=$7.23\times10^{-11}$ mol $L^{-1}$). MPs 16, 18, and 21 show lower $EC_{50}$ than MPs 19 and 20. MP17 was the less active analog with the highest $EC_{50}$ value of $4.35\times10^{-6}$ mol $L^{-1}$.

Among the previously described MPs (Jamil et al., 2018), MP1 (structure reproduced below from Jamil et al., 2018) was the most potent SL analog ($EC_{50}$=$1.5\times10^{-9}$ mol $L^{-1}$). This $EC_{50}$ value of MP1 was about 17 times higher than that of GR24. In the present study, $EC_{50}$ value of MP16 ($EC_{50}$=$1.05\times10^{-10}$ mol $L^{-1}$) is less than two times higher than that of GR24 ($EC_{50}$=$7.23\times10^{-11}$ mol $L^{-1}$). The simple synthesis route of MP16 will more than compensate the slightly lower activity of this compound, in comparison to GR24.

MP1

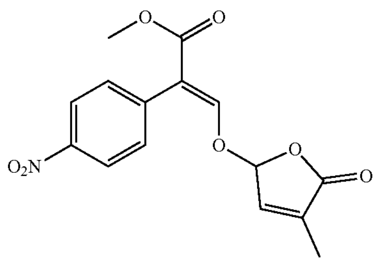

Example 6. The Hydrolysis Rate of SL Analogs by SL Receptor Demonstrates their Activity in Inducing Seed Germination Materials and Methods In Vitro YLG (Yoshimulactone Green) Assays Purification of ShHTL7/OsD14 was carried out by adopting the procedure explained previously (Jamil et al., 2018). In vitro YLG hydrolysis assays were conducted as described before (Tsuchiya et al., 2015). About 3.0 μM of purified ShHTL7/OsD14 protein was used in a reaction buffer (1×PBS buffer, pH 7.3) with 0.1% dimethyl sulfoxide (DMSO) at a 100 μl volume on a 96-well black plate (Greiner). SL analogs (at range between 0.01 to 50 μM) were co-incubated with 1.0 μM of YLG (Tokyo Chemical Industry Co. Ltd., product number E1238) for 60 min at room temperature. In this competition assay, fluorescent intensity was measured by spectraMax i5 (Molecular Devices) at excitation at 480 nm and detection at 520 nm. The variation in fluorescence recorded over the course of 1 h of YLG incubation in protein-free buffer was subtracted from the data collected in presence of protein. $IC_{50}$ values were calculated by using Quest Graph™ $IC_{50}$ Calculator.

Results

Figure 8A:
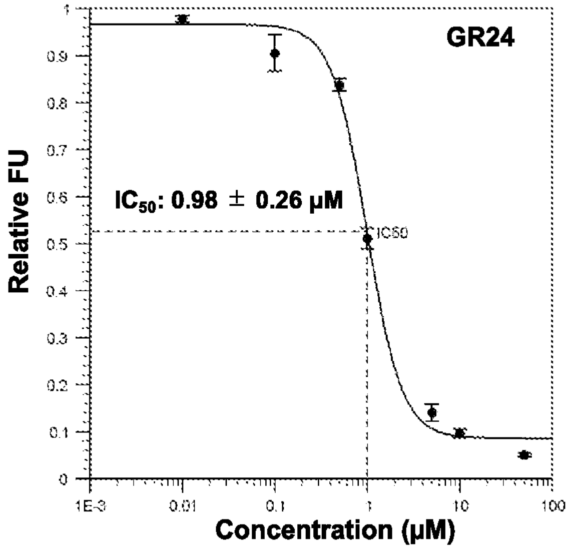
FIGS. 8A-8B are graphs showing Yoshimulactone Green (YLG) hydrolysis of GR24 (FIG. 8A) and MP16 (FIG. 8B) by ShHTL7. Seven concentrations of MP16 and GR24 ranging from 0.01, 0.1, 0.5, 1.0, 10 and 50 μM were applied, and YLG fluorescent intensity was measured (with or without purified ShHTL7). Values represent means±SE (n=3).
Figure 8B:
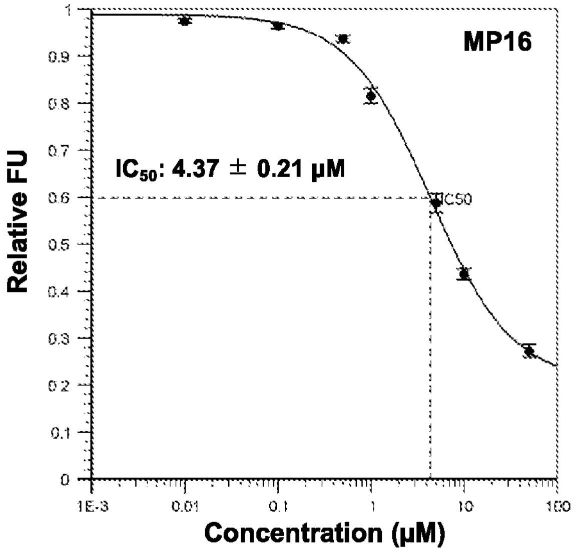
Figure 9A:
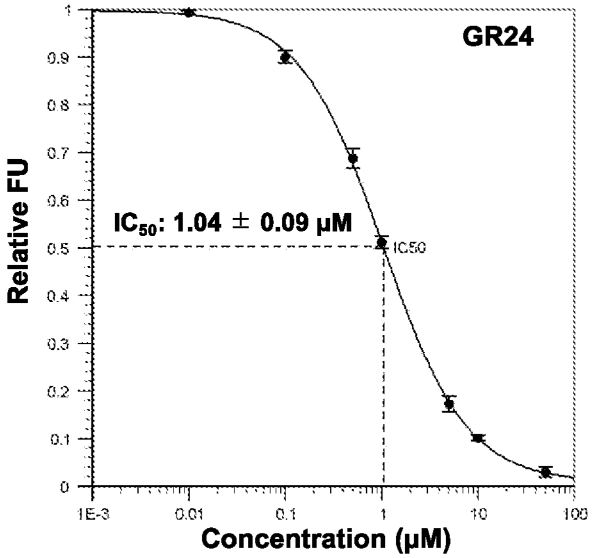
FIGS. 9A-9B are graphs showing YLG hydrolysis of GR24 (FIG. 9A) and MP16 (FIG. 9B) by OsD14. Seven concentrations of MP16 and GR24 ranging from 0.01, 0.1, 0.5, 1.0, 10 and 50 μM were applied, and YLG fluorescent intensity was measured (with or without purified OsD14). Values represent means±SE (n=3).
Figure 9B:
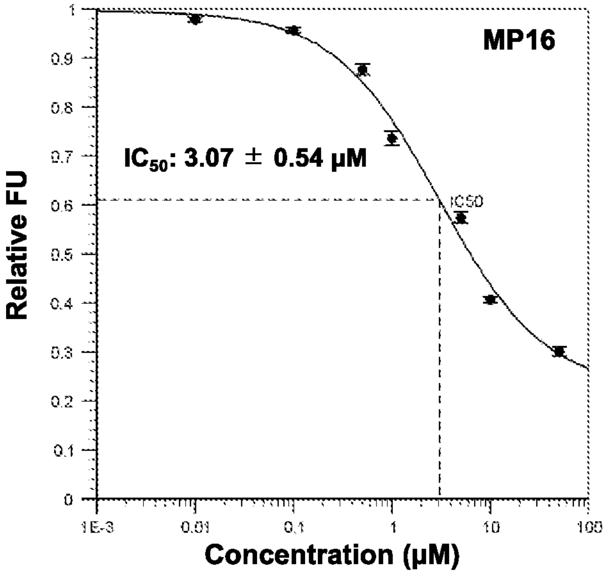

The hydrolysis rate of SLs by the *Striga* SL receptor ShHTL7 is related to their activity in inducing seed germination. The hydrolysis rate of MP16 by ShHTL7 (*Striga hermonthica* Hyposensitive to Light) (Toh et al., 2015), the most sensitive SL receptor in *Striga* seeds, and the rice SL receptor OsD14 (Arite et al., 2009; Yao et al., 2016) was measured by conducting the competitive. The hydrolysis rate of MP16 ($IC_{50}$: 4.37±0.21 μM) by ShHTL7 was lower than that of GR24 ($IC_{50}$: 0.98±0.26 μM) (FIGS. 8A-8B). In competition with YLG in OsD14-mediated hydrolysis assays, GR24 was hydrolyzed more efficiently ($IC_{50}$: 1.04±0.09 μM) than MP16 ($IC_{50}$: 3.07±0.54 μM) (FIGS. 9A-9B). MP16 showed a growth inhibitory and senescence effect on rice seedlings, but the OsD14-mediated YLG hydrolysis assays show that it is a less preferred substrate compared to GR24. This result shows that some other elements, such as stability, transport and SL uptake could also be involved in the growth retarding activity of MP16 (FIGS. 8A-8B and 9A-9B).

In conclusion, the disclosed SL analogs can help understanding the different functions of SLs, and have a large application potential in agriculture, particularly in combating root parasitic weeds.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

Abe, et al. (2014). *PNAS* 111, 18084-18089.
Abuauf, et al (2018). *Plant Science* 277, 33-42.
Agusti, et al. (2011). *PNAS* 108, 20242-20247.
Akiyama, et al. (2005). *Nature* 435, 824-827.
Al-Babili, et al. (2015). *Annual Review of Plant Biology* 66, 161-186.Alder,
A., Jamil, et al. (2012). *Science* 335, 1348-1351.
Arite, et al. (2009). *Plant and Cell Physiology* 50, 1416-1424
Bonfante, et al. (2010). *Nature Comm* 1, 48. doi: 10.1038/ncomms1046
Boyer, et al. (2014). *Molecular Plant* 7, 675-690. doi: 10.1093/mp/sst163
Bruno, et al. (2016). *Planta* 243, 1429-1440.
Bruno, et al. (2014). *Febs Letters* 588, 1802-1807.
Bruno, M., et al. (2017). *FEBS letters* 591, 792-800.
Charnikhova, et al. (2017). *Phytochemistry* 137, 123-131.
Charnikhova, et al. (2018). *Phytochemistry Letters* 24, 172-178. Cook, et
al. (1966). *Science* 154, 1189-1193.
Decker, et al. *New Phytologist* 216, 455-468.
Ejeta, (2007). *Crop Science* 47, 216-227.
Fukui, et al. (2013). *Molecular Plant* 6, 88-99.
Fukui, et al. (2011). *Bioorg & Med Chem Lett.* 21, 4905-4908.
Gomez-Roldan, et al. (2008). *Nature* 455, 189-194.
Gressel, et al. (2004). *Crop Protection* 23, 661-689.
Gutjahr, et al. (2013). *Ann. Rev. Cell and Dev. Biol.* 29. 93-617
Ha, et al. (2014). *PNAS* 111, 851-856.
Jamil, et al. (2012). *Field Crops Research* 134, 1-10.
Jamil, et al. *Journal of Experimental Botany* 69, 62319-62331.
Jia, et al. (2016). *Molecular Plant* 9, 1341-1344.
Jia, et al. *Journal of Experimental Botany* 69, 2189-2204.
Johnson, et al. *Journal of the Chemical Society* 1, 1734-1743.
Kapulnik, et al. (2011). *Planta* 233, 209-216.
Kgosi, et al. (2012). *Weed Research* 52, 197-203.
Kondo, et al. (2007). *Bioscience Biotech. and Biochem.y* 71, 2781-2786.
Kountche, et al. (2019)., *People, Planet* 1, 107-118.
Lachia, et al. *Bioorganic & Medicinal Chemistry Letters* 25, 2184-2188.
Mangnus, et al. (1992). *Journal of Agric. and Food Chem.* 40, 1066-1070.
Mangnus, et al. (1992a). *J. of Agric. and Food Chem.* 40, 1230-1235.
Mangnus, et al. (1992b). *J. of Agric.l and Food Chem.* 40, 1222-1229
Rasmussen, et al. (2013). *Molecular plant* 6, 100-112.
Rodenburg, et al. (2016). *Agric., Ecosystems & Environ.* 235, 306-317.
Rubiales, et al. (2009). *Weed Research* 49, 23-33
Ruyter-Spira, et al. (2011). *Plant Physiology* 155, 721-734.
Samejima, et al. (2016). *Pest Management Science* 72, 2035-2042.
Scaffidi, et al. (2014). *Plant Physiology* 165, 1221-1232.
Seto, et al. (2014). *PNAS* 111, 1640-1645.
Toh, et al. (2015). *Science* 350, 203-207.
Tsuchiya, et al. (2015). *Science* 349, 864-868
Ueno, et al. (2014). *Phytochemistry* 108, 122-128.
Umehara, et al. (2008). *Nature* 455, 195-200.
Waters, et al. (2017 *Annual Review of Plant Biology* 68, 291-322.
Wigchert, et al. (1999). *Journal of Agric. and Food Chem.* 47, 1705-1710.
Yamada, et al. (2014). *Planta* 240, 399-408.
Yao, et al. (2016). *Nature* 536, 469-473.
Yasui, et al. (2017). *Nature Communications* 8, 674-683.
Zhang, et al. (2014). *Nature Chemical Biology* 10, 1028-1033.
Zwanenburg, et al. (2009). *Pest Management Science* 65, 478-491.
Zwanenburg, et al. (2013). *Bioorganic & Med. Chem. Lett.* 23, 5182-5186.
Zwanenburg, et al. (2013). *Molecular Plant* 6, 38-62.
Zwanenburg, et al. (2016a). *Pest Manag. Science* 72, 2016-2025.
Zwanenburg, et al. (2016b). *Planta* 243, 1311-1326.
Zwanenburg, et al. *Pest Management Science* 72, 15-29.

We claim:

1. A compound having the structure of Formula I:

Formula I

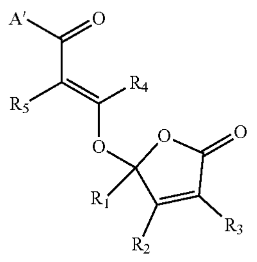

(a) wherein A' is an alkoxy group containing one substituent, an amino group optionally containing one or two substituents at the amino nitrogen, or a thiol group optionally containing one substituent at the thiol sulfur;

(b) wherein $R_1$-$R_4$ are independently a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group; and (c) wherein $R_5$ is an unsubstituted alkyl group, a substituted alkyl group, an unsubstituted cycloalkyl group, a substituted cycloalkyl group, an unsubstituted heteroalkyl group, a substituted heteroalkyl group, an unsubstituted cycloheteroalkyl group, a substituted cycloheteroalkyl group, an unsubstituted alkenyl group, a substituted alkenyl group, an unsubstituted heteroalkenyl group, a substituted heteroalkenyl group, a substituted alkynyl group, a substituted heteroalkynyl group, an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, or a substituted polyheteroaryl group, an unsubstituted alkylaryl group, or a substituted alkylaryl group.

2. The compound of claim 1 having the structure of Formula II:

Formula II

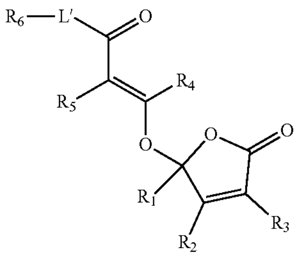

(a) wherein $R_1$-$R_4$ are as defined in claim 1;

(b) wherein L' is an oxygen atom or a sulfur atom; and (c) wherein $R_5$ and $R_6$ are independently an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group, wherein the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

3. The compound of claim 1 having the structure of Formula III:

Formula III

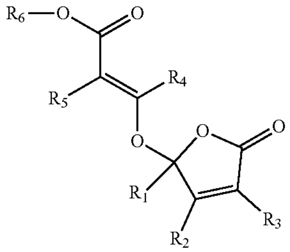

(a) wherein $R_1$-$R_4$ are independently a hydrogen atom, a halogen atom, an alkyl group, a hydroxyl group, or an amino group;

(b) wherein $R_5$ and $R_6$ are independently an unsubstituted aryl group, a substituted aryl group, an unsubstituted polyaryl group, a substituted polyaryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

4. The compound of claim 1 having the structure of Formula IV:

Formula IV

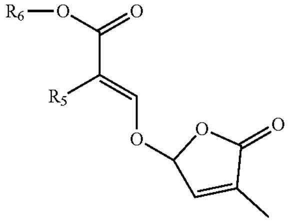

(a) wherein $R_5$ is an unsubstituted aryl group or a substituted aryl group; and (b) wherein $R_6$ is an unsubstituted aryl group, a substituted aryl group, an unsubstituted polyaryl group, a substituted polyaryl group, an unsubstituted alkylaryl group, or a substituted alkylaryl group, wherein the substituents are independently a halogen atom or an alkyl group.

5. The compound of claim 1 having the structure of Formula V:

Formula V

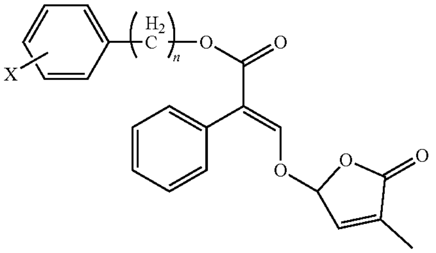

(a) wherein n is 0 or a positive integer between 1 and 5; and (b) wherein X is a hydrogen atom, a halogen atom, or an alkyl group.

6. The compound of claim 1, wherein $R_5$ is an unsubstituted aryl group, and $R_6$ is an unsubstituted polyaryl group.

7. The compound of claim 1 having the structure of Formula VI:

Formula VI

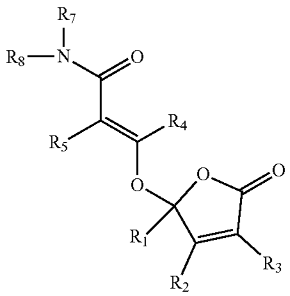

(a) wherein $R_1$-$R_4$ are as defined in claim 1;

(b) wherein $R_5$ is an unsubstituted aryl group, a substituted aryl group, an unsubstituted heteroaryl group, a substituted heteroaryl group, an unsubstituted polyaryl group, a substituted polyaryl group, an unsubstituted polyheteroaryl group, substituted polyheteroaryl group, an unsubstituted alkylaryl group, or a substituted alkylaryl group; and (c) wherein $R_7$ and $R_8$ are independently a hydrogen atom, an unsubstituted alkyl group, a substituted alkyl group, an unsubstituted heteroalkyl group, a substituted heteroalkyl group, an unsubstituted alkenyl group, a substituted alkenyl group, an unsubstituted heteroalkenyl group, a substituted heteroalkenyl group, an unsubstituted alkynyl group, a substituted alkynyl group, an unsubstituted heteroalkynyl group, a substituted heteroalkynyl group, an unsubstituted aryl group, a substituted aryl group, an unsubstituted an unsubstituted heteroaryl group, or a substituted heteroaryl group, wherein the substituents are independently a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an alkoxy group, an acyl halide group, a carboxylic acid group, a carboxylate group, an alkyl group, a heteroalkyl group, an alkenyl group, a heteroalkenyl group, an alkynyl group, a heteroalkynyl group, an aryl group, a heteroaryl group, polyaryl group, a heteropolyaryl group, a alkylaryl group, an amino group, an ester group, a hydroxyl group, a thiol group, a sulfonyl group, an amide group, an azo group, an acyl group, a carbonyl group, a carbonate ester group, an ether group, an aminooxy group, or a hydroxyamino group.

8. The compound of claim 7, (a) wherein $R_1$-$R_4$ are independently a hydrogen atom, a halogen atom, an alkyl group, a hydroxyl group, or an amino group;

(b) wherein $R_5$ is an unsubstituted aryl group, a substituted aryl group, an unsubstituted polyaryl group, a substituted polyaryl group, an unsubstituted alkylaryl group, or a substituted alkylaryl group; and (c) wherein $R_7$ and $R_8$ are independently a hydrogen atom, an unsubstituted alkyl group, a substituted alkyl group, an unsubstituted heteroalkyl group, a substituted heteroalkyl group, an unsubstituted aryl group, a substituted aryl group, an unsubstituted heteroaryl group, a substituted heteroaryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

9. The compound of claim 7 having the structure of Formula VII:

Formula VII

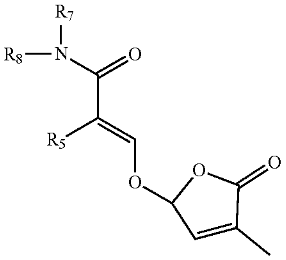

(a) wherein $R_5$ is an unsubstituted aryl group or a substituted aryl group; and (b) wherein $R_7$ and $R_8$ are independently a hydrogen atom, an unsubstituted alkyl group, a substituted alkyl group, an unsubstituted aryl group, a substituted aryl group, an unsubstituted alkylaryl group, or a substituted alkylaryl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

10. The compound of claim 7 having the structure of Formula VIII:

Formula VIII

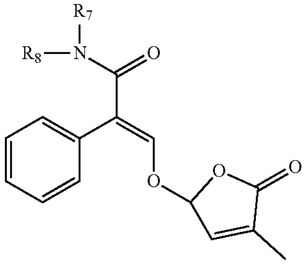

wherein $R_7$ and $R_8$ are independently a hydrogen atom, an unsubstituted alkyl group, or a substituted alkyl group, wherein the substituents are independently a halogen atom, a nitrile group, an isonitrile group, a nitro group, an aldehyde group, an alkoxy group, a carboxylic acid group, an alkyl group, an amino group, an ester group, a hydroxyl group, a thiol group, or an ether group.

11. A compound having a structure of:

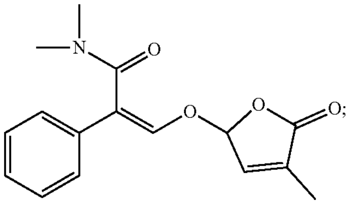

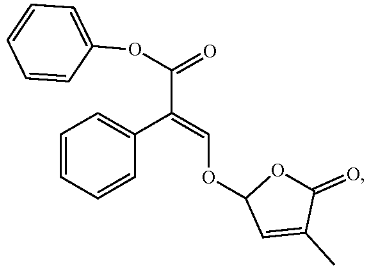

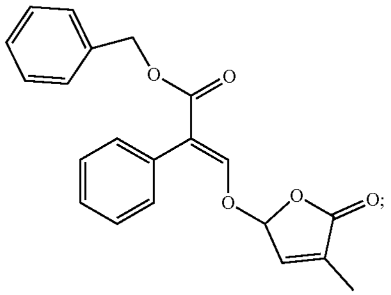

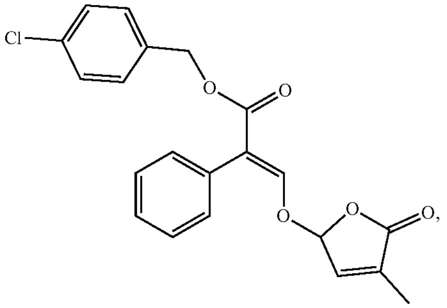

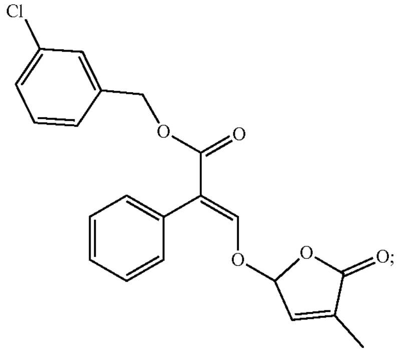

-continued

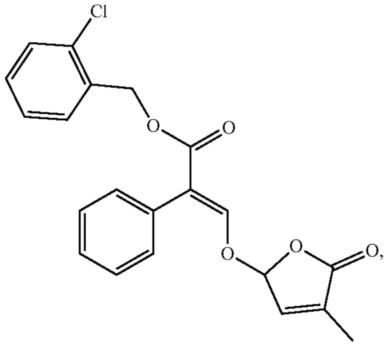

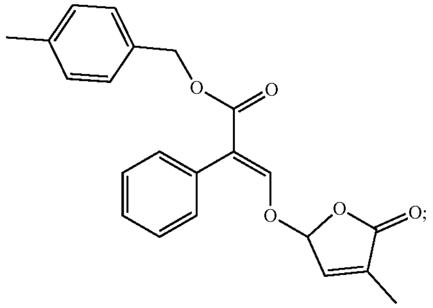

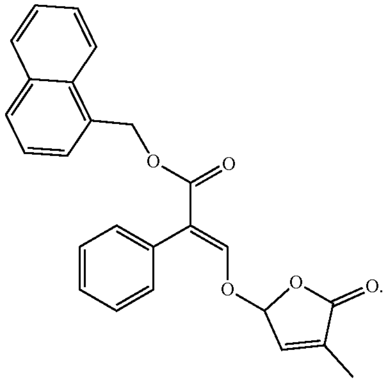

12. A method of regulating plant growth comprising applying one or more formulations to a plant, a plant part, or a growing site of plant, wherein the one or more formulations comprise:

(a) one or more compounds of claim 1, or salts thereof, and (b) one or more formulation excipients, wherein the one or more compounds or salts thereof are in an effective amount to regulate plant growth.

13. The method of claim 12, wherein the one or more compounds or salts thereof are in an effective amount to inhibit tillering of the plant.

14. The method of claim 12, wherein the one or more compounds or salts thereof are in an effective amount to trigger dark-induced leaf senescence.

15. A method of combating root parasitic plants comprising applying one or more formulations to a root parasitic plant, a plant part of root parasitic plant, or a growing site of root parasitic plant, in the absence of the root parasitic plant's host plant, wherein the one or more formulations comprise:

(a) one or more compounds of claim 1, or salts thereof, and (b) one or more formulation excipients, wherein the one or more compounds or salts thereof are in an effective amount to induce seed germination of the root parasitic plant.

* * * * *